(12) United States Patent
Veloz et al.

(10) Patent No.: US 10,328,168 B1
(45) Date of Patent: Jun. 25, 2019

(54) METHOD AND APPARATUS FOR OPERATING A GERMICIDAL UV DEVICE WITH A PROGRAMMABLE LOGIC CONTROLLER AND A BLUETOOTH LOW ENERGY SOLUTION

(71) Applicants: Peter Veloz, Glendale, CA (US); Ashish Mathur, Santa Clarita, CA (US); Aleksandr Shostak, Northridge, CA (US); Richard Hayes, Thousand Oaks, CA (US); David Witham, Ventura, CA (US); Mitch Babkes, Santa Clarita, CA (US); Filiberto Betancourt, North Hills, CA (US); Lev Rotkop, Beverly Hills, CA (US); Stuart Tyrrell, Los Altos, CA (US); Walt Maclay, Sunnyvale, CA (US); Dan Brown, San Jose, CA (US)

(72) Inventors: Peter Veloz, Glendale, CA (US); Ashish Mathur, Santa Clarita, CA (US); Aleksandr Shostak, Northridge, CA (US); Richard Hayes, Thousand Oaks, CA (US); David Witham, Ventura, CA (US); Mitch Babkes, Santa Clarita, CA (US); Filiberto Betancourt, North Hills, CA (US); Lev Rotkop, Beverly Hills, CA (US); Stuart Tyrrell, Los Altos, CA (US); Walt Maclay, Sunnyvale, CA (US); Dan Brown, San Jose, CA (US)

(73) Assignee: ULTRAVIOLET DEVICES, INC., Valencia, CA (US)

( * ) Notice: Subject to any disclaimer, the term of this patent is extended or adjusted under 35 U.S.C. 154(b) by 9 days.

(21) Appl. No.: 15/608,943

(22) Filed: May 30, 2017

Related U.S. Application Data

(63) Continuation-in-part of application No. 15/044,103, filed on Feb. 15, 2016, now Pat. No. 9,666,242.

(51) Int. Cl.
| | |
|---|---|
| *A61L 2/10* | (2006.01) |
| *A61L 9/20* | (2006.01) |
| *H05K 7/20* | (2006.01) |
| *H01J 61/52* | (2006.01) |
| *H04W 4/00* | (2018.01) |
| *H04W 4/80* | (2018.01) |

(52) U.S. Cl.
CPC ............... *A61L 2/10* (2013.01); *A61L 9/20* (2013.01); *H01J 61/52* (2013.01); *H04W 4/80* (2018.02); *H05K 7/20436* (2013.01)

(58) Field of Classification Search
CPC . A61L 2/00; A61L 2/0029; A61L 2/08; A61L 2/10; A61L 9/20; H01J 61/52; H05K 7/20436
USPC ..... 250/493.1, 494.1, 504 R; 422/20, 21, 22, 422/24
See application file for complete search history.

(56) References Cited

U.S. PATENT DOCUMENTS 9,666,424 B1 * 5/2017 Veloz ..................... H01J 61/52

* cited by examiner

*Primary Examiner* — Nicole M Ippolito
(74) *Attorney, Agent, or Firm* — Law Office of David Hong

(57) ABSTRACT

This invention employs a computer system or a programmable logic controller (computer) with a specific wireless communication protocol (BLE) to allow for remote connectivity of the germicidal UV device to display the status of the disinfection cycle and to operate the device and send and transfer data wirelessly to the Cloud via the BLE interface. A dose sensitive coupon, which can undergo color change in response to UV dosage, can also be used.

10 Claims, 22 Drawing Sheets

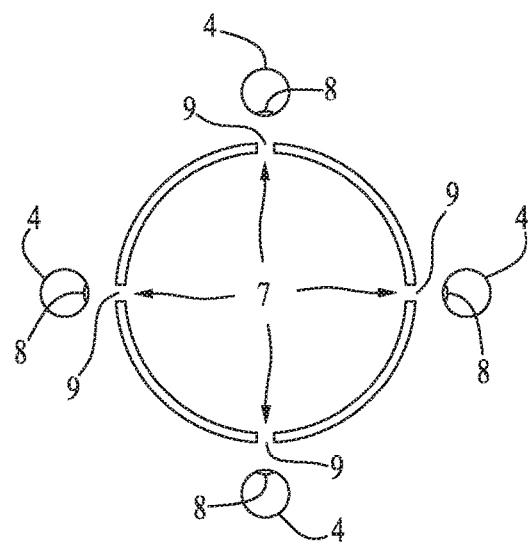
fig. 3A
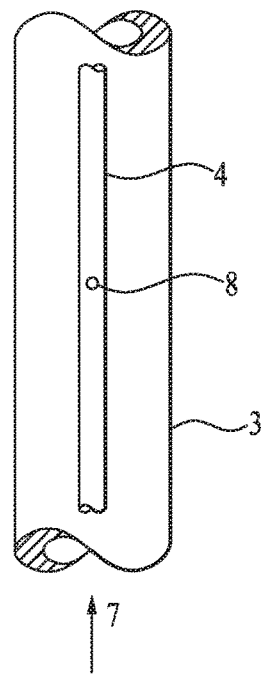 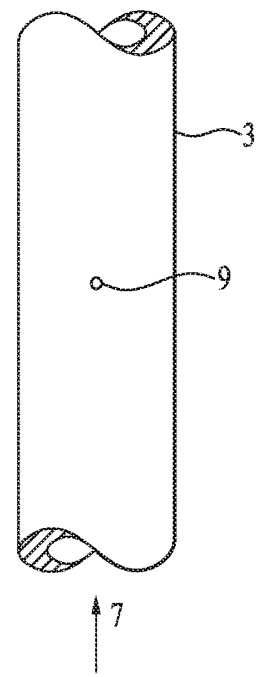
fig. 3B  fig. 3C

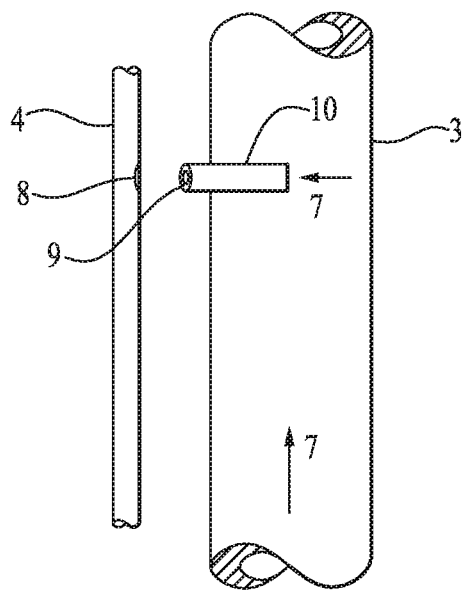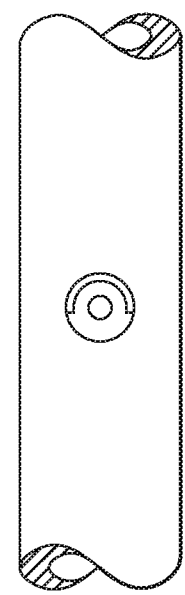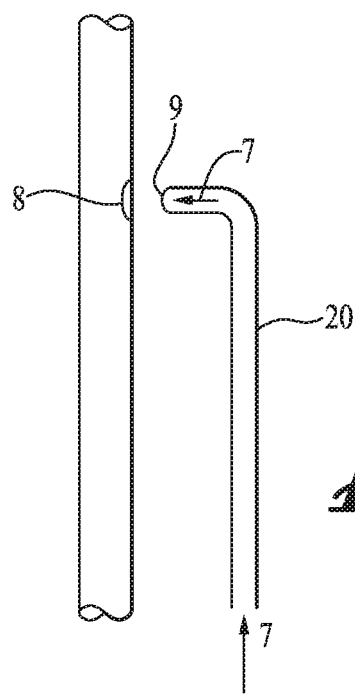
FIG. 4A  FIG. 4B
FIG. 4C

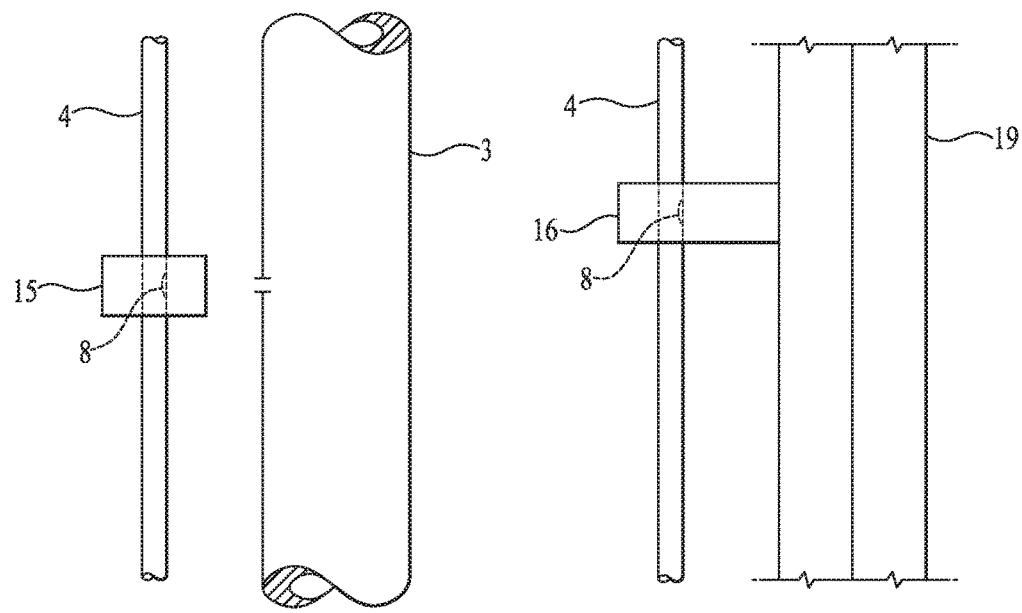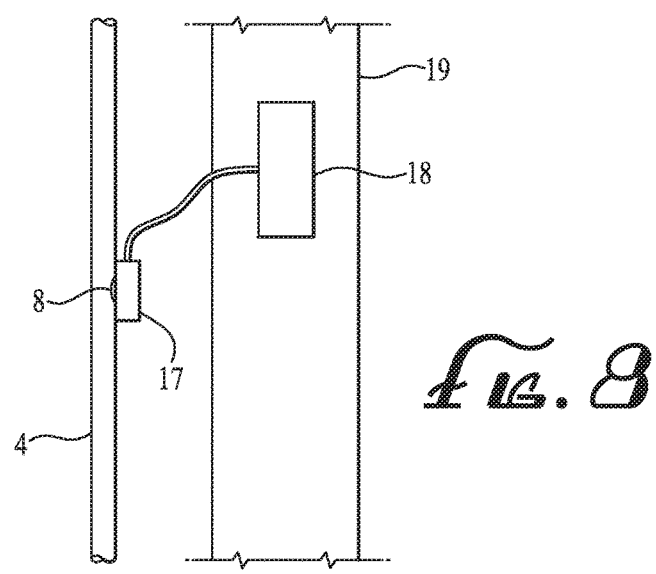

An overview of the architecture is as follows:

METHOD AND APPARATUS FOR OPERATING A GERMICIDAL UV DEVICE WITH A PROGRAMMABLE LOGIC CONTROLLER AND A BLUETOOTH LOW ENERGY SOLUTION

PRIORITY CLAIM

This application is a continuation in part of U.S. patent application Ser. No. 15/044,103, filed on Feb. 15, 2016, and issues as U.S. Pat. No. 9,666,424 on May 30, 2017, which is a continuation in part of U.S. patent application Ser. No. 14/325,357, filed on Jul. 7, 2014, and issued as U.S. Pat. No. 9,265,174 on Feb. 16, 2016, which claims the benefit of U.S. Provisional Patent Appl. No. 61/895,010, filed on Oct. 24, 2013; this application also claims the benefit of U.S. Provisional Patent Appl. No. 62/220,932, filed on Sep. 18, 2015; this application is also related to U.S. Design Pat. D684,671, which was issued on Jun. 19, 2013; this application is also related to U.S. Provisional Patent Appl. No. 61/761,670, filed on Feb. 6, 2013 and U.S. patent application Ser. No. 14/172,886, filed on Feb. 4, 2014; all mentioned applications and patents are incorporated by reference in entirety.

BACKGROUND OF THE INVENTION

The effectiveness of germicidal ultraviolet (UV-C) irradiation as a powerful disinfecting technology has been well documented in peer-reviewed literature as well as in practice. Germicidal UV-C disinfection has been used for decades in disinfecting municipal drinking water, waste water, and in air and surface applications to disinfect against various micro-organisms such as bacteria, virus and mold. UVC devices employ one or more lamps emitting a spectral wavelength output of approximately 254 nm which disrupts the DNA structure of the micro-organisms, rendering them harmless and unable to reproduce.

The lamps typically used in these devices are low pressure mercury vapor discharge lamps. There are three basic types of low pressure ultraviolet lamps in commercial use. A standard output lamp, with input of approximately 425 milliamps has been used for many years. For about two decades, a higher output type lamp with an input of about 850 milliamps has been utilized. Recently a very high output lamp with an input current of from 2.0 to as high as 8.0 amps has become popular in some types of disinfection application. Applications of this type of lamp are popular where high levels of UVC are required such as in municipal water treatment plants.

Construction of the lamp and the materials used are somewhat different to accommodate the high temperatures. With the standard and high output lamps, pure mercury is generally used in the lamp to generate the UVC wavelength of approximately 254 nm. In the very high output lamp, generally the mercury is supplied in an amalgam of metals and may be located on one or more spots placed on the inside of the lamp envelope.

The necessary relatively high doses of ultraviolet radiation typically required to achieve desired disinfection levels requires the use of multiple germicidal lamps. The use of multiple germicidal lamps increases expenses, as well as maintenance. Therefore, it is desirable to use fewer very high output germicidal lamps.

However, applying a very high output germicidal lamp, particularly in air, is not without difficulties. During operation of a low pressure mercury vapor discharge lamp, the vapor pressure of the mercury greatly affects lamp output. For an efficient operation of the lamp, a predetermined range of the mercury vapor pressure inside the discharge vessel is required.

By using an amalgam containing mercury, the mercury vapor pressure can be controlled within this predetermined range for a relatively broad temperature range, allowing operating the lamp at a high efficiency and to deliver a relatively high radiation output within this temperature range. Very high output amalgam lamps thus provide the highest UVC output amongst low pressure mercury lamps and are therefore highly desirable for use for disinfection applications.

The mercury or amalgam of mercury may be located in many different places. In many lamps, it is typically located in one or more locations of the glass inner surface facing the discharge space of the low-pressure mercury vapor discharge lamp. As a result, the amalgam is exposed directly to the discharge space so that the temperature of the amalgam can increase relatively rapidly after the discharge lamp is turned on or lit up. The ideal operating temperature range for germicidal amalgam lamps can vary due to the composition of the amalgam. Typically, it is from 80 degrees C. to 140 degrees C. However, the higher temperatures occurring at high loading of the lamp may cause the temperature of the amalgam to exceed the maximum operating temperature. This high temperature is not generally a problem when very high output lamps are used for water treatment. In this application, the lamps are generally housed in a quartz sleeve and submerged in moving water, which allows cooling of the lamp and maintains the temperature within the proper temperature range. This is most likely the reason that most applications of very high output lamps are limited to water treatment applications only.

Currently, there are little or no applications of very high output lamps in ambient air. In this air application, the temperature at the amalgam spot can exceed 150 degrees C. If the amalgam melts, several things may happen. The amalgam may move out of position and could make contact with an electrode and cause possible shorting or ineffective operation of the lamp. The molten amalgam material may be spread throughout the lamp and solidify at those positions when the operating conditions change. Solidified amalgam material at a position within the discharge path, for example, may become too hot at a later stage of the lamp use, i.e. the amalgam temperature will become outside its temperature range. When the amalgam is operating outside its ideal temperature range, this results in too high a mercury vapor pressure and hence reduces the lamp efficiency.

The positioning of the (germicidal) lamp, i.e. horizontal versus vertical positioning of the lamp, also influences the temperature of the amalgam. If the system design and application do not allow the amalgam to get into their proper operating temperature range, the lamp will have very low UV output and tend to be quite unstable.

Amalgam lamps provide the highest UVC output amongst low pressure mercury lamps and are therefore highly desirable for use in disinfection applications. However, due to the susceptibility of the amalgam to melt when the temperature exceeds the operating range, the use of germicidal amalgam lamps has been almost exclusively limited to water or liquid disinfection applications, wherein the amalgam lamps are constantly submerged in water or liquids, allowing the lamps to operate in the ideal temperature range.

It is the purpose of this invention to solve these temperature problems for air and surface disinfection applications.

SUMMARY OF THE INVENTION

It is highly desirable to be able to utilize germicidal lamps and in particular very high output germicidal lamps for air and surface applications. The present invention discusses a novel approach to utilize the very high UVC output of germicidal amalgam lamps in UVC disinfection devices in air and surface applications by providing a means to reduce and/or control the temperature of the amalgam spot(s) thus allowing the lamp to operate in its ideal operating range.

In another embodiment of the application, there is a PLC with BLE hardware and software solution that can be integrated with the PLC and HMI system on the UV device in order to communicate with the UV device wirelessly and transmit the data to a controlled Cloud based server.

Another object of this invention is to allow the use of the germicidal amalgam lamp for use in a vertical configuration in a UVC disinfection device by ensuring that the amalgam is kept in its position and operating within the ideal temperature range. Yet another object of this invention is to reduce or eliminate the possibility of the amalgam melting. The present invention allows the germicidal amalgam lamps to be used in devices for air and surface disinfection where the amalgam lamp is exposed to ambient air. The invention discloses a novel approach to cool and/or control the temperature of the amalgam spot, thereby preventing the amalgam spot from melting and allowing the lamp to operate in an ideal operating temperature range and deliver maximum UVC output.

An example of a UVC disinfection device is the V-360+ mobile disinfection device, by UltraViolet Devices, Inc., which is used to disinfect surfaces in a healthcare environment. It is therefore highly desirable to utilize amalgam lamps to maximize the UVC output of the V360+ device and allow rapid disinfection times. The V-360+ device (See FIG. 1) utilizes more than one or four germicidal amalgam lamps which are located around a highly reflective hollow cylindrical aluminum support/conduit mounted at the center of a circular base. The combination of the high output amalgam lamps and the highly reflective support allows the V360+ device to deliver a high dose of UVC in order to achieve high levels of disinfections and rapid disinfection times.

However, with the lamps positioned in a vertical configuration, the amalgam spots are highly susceptible to overheating and even melting and moving out of position due to conditions described previously.

When the device is used in a typical ambient environment, the temperature of the critical spots (amalgam) can exceed 150 degrees C. and make the lamp operate outside its ideal operating range. The proximity of these lamps to the aluminum support lends to even higher temperature at the amalgam spot or spots.

This invention overcomes this challenge by providing an effective method to control the temperature of the critical spot(s) of the lamps on this device. In one embodiment of the application, the temperature of the critical spot (amalgam) is maintained by directing a uniform flow of air on and around the critical spot or spots (amalgam). The flow of air is generated by a fan located inside the V-360+, whereby the flow of air is directed to the critical spot (amalgam) through apertures located on the cylindrical conduit in close proximity to the spot or spots. The size of the cooling fan, location on the cylindrical conduit and the size of the apertures are judiciously chosen to provide an optimal amount of air flow through the apertures on the cylindrical conduit.

The air flow obtained through this arrangement is such that it provides an optimal amount of cooling in order maintain the temperature of the amalgam spot or spots in the ideal operating range, approximately between 80 deg C. and 140 deg C.

In another embodiment of the application, air flow is provided to the amalgam spot or spots through the use of air distribution nozzles that are mounted on the support and/or conduit in close proximity to the critical spot or spots, wherein the air flow is generated by the fan located optimally inside the device.

In another embodiment of the application, air flow is provided to the amalgam spot(s) via air diverter tubes that are mounted inside the support/conduit in close proximity to the amalgam spot or spots and divert an optimal amount of air onto the amalgam spot or spots.

In another embodiment of the application, the temperature of the critical spot or points is controlled by the use of a heat sink that is mounted on the critical spot or points and is connected to the support. By transferring the excess heat to the support, the heat sink maintains the temperature of the critical spot or spots (amalgam) in the desired operating range.

In yet another embodiment, a thermoelectric device is affixed to the critical spots (amalgam) of the lamp and is used to control the temperature of the critical spot. The thermoelectric device may be controlled to maintain a pre-determined temperature, within the ideal temperature range. A temperature sensing device may also be used by the controller.

BRIEF DESCRIPTION OF THE DRAWINGS

FIG. 3*a*. A horizontal cross sectional view of the device shown in FIG. 1 (enlarged).

FIG. 3*b*. An enlarged portion of the conduit 3, shown in FIG. 2.

FIG. 3*c*. The view shown in FIG. 3*b* with the lamp 8 removed for clarity.

FIG. 4*a*. A view of an alternate embodiment showing use of an additional component to direct air.

FIG. 4*b*. A view of the additional component of FIG. 4*a* from inside the conduit 3.

FIG. 4*c*. A view of an individual conduit (alternate embodiment)

FIG. 6. A side view of an alternate embodiment incorporating heat sinks attached to the UV lamp.

FIG. 7. A side view of an alternate embodiment with a heat sink attached to the UV lamp and in contact with a structural member.

FIG. 8. A view of a solid state thermoelectric device attached to the UVC lamp.

PARTS LISTING FOR FIGS. 22-25

Figure 1:
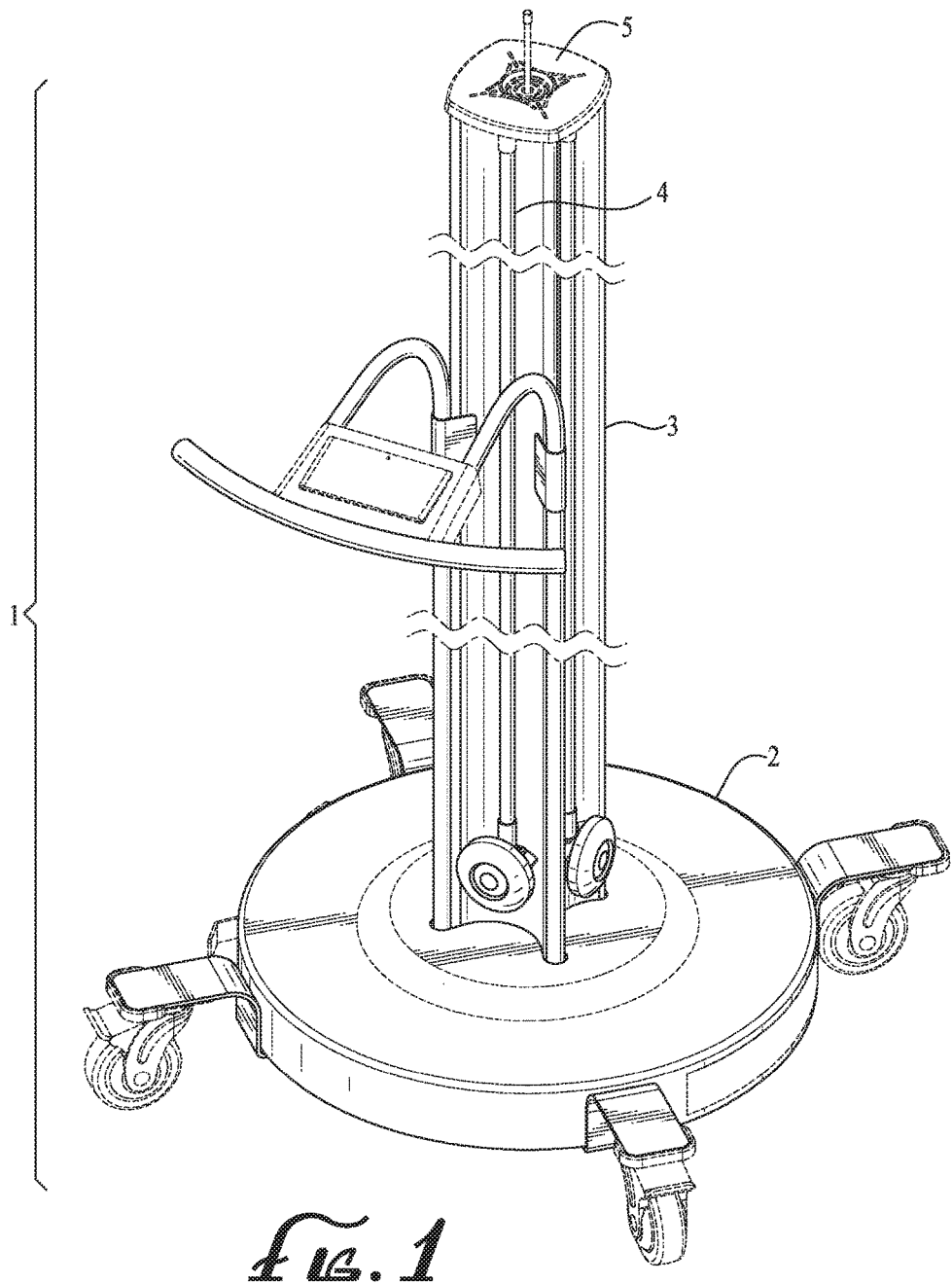
FIG. 1. An isometric drawing of one preferred embodiment of the UVC device utilizing this invention.

10 UVC light generating device
15 room
20 table
25 bed
30 door
35 UVC Dose Verify card and coupon
40 UV Sensitive Area on card
45 UV Reference area on card

DETAILED DESCRIPTION OF THE INVENTION

Referring to FIG. 1, a typical device 1 for the UV disinfection of air or surfaces is shown. The basic elements of the device are a base 2, a support, in this case, acting also as a conduit 3 and an opening 5 for the exit of air. One or more lamps 4 are installed around the support or conduit 3.

Figure 2:
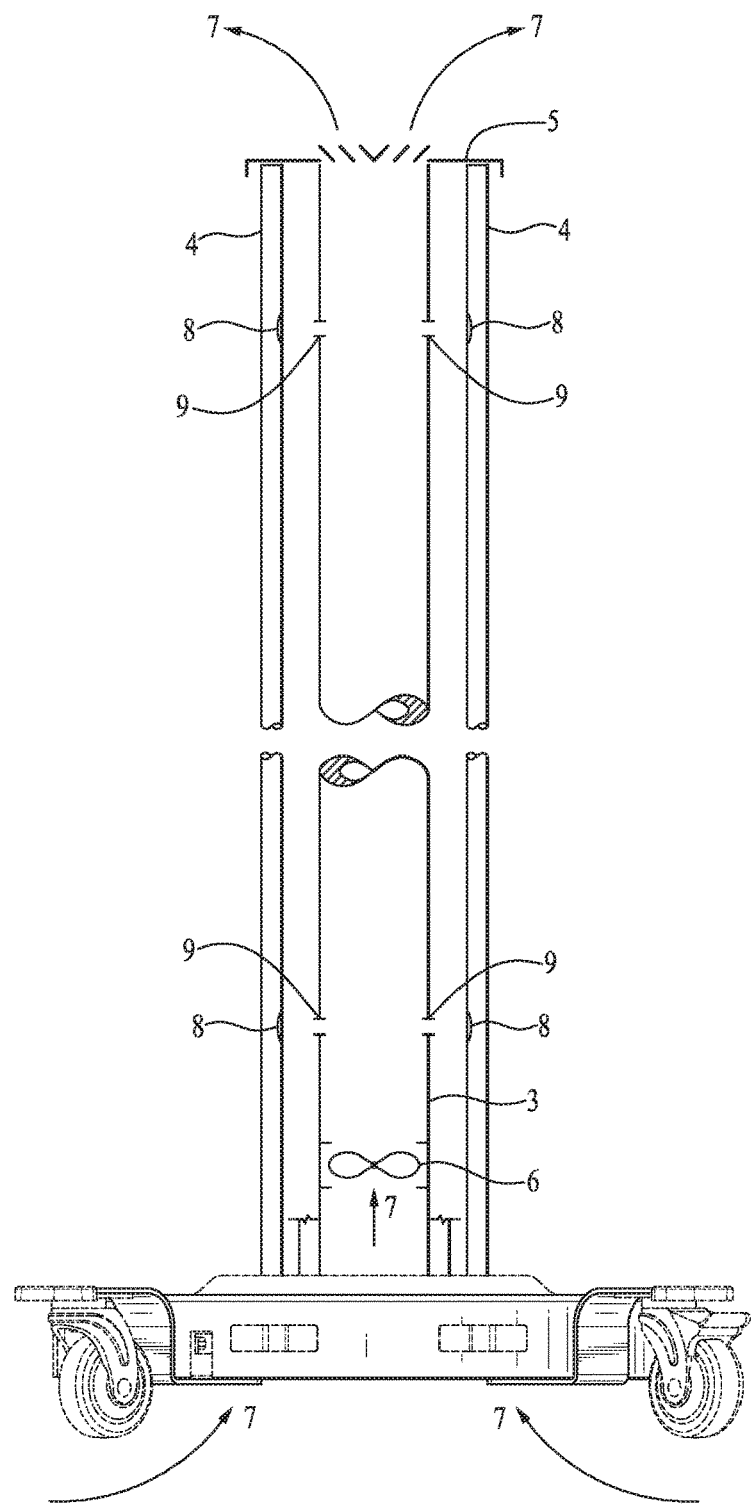
FIG. 2. A vertical cross sectional view of the device shown in FIG. 1

FIG. 2 shows the typical device 1, in cross section. An air moving device 6, including without limitation a fan or blower, is installed in the conduit 6 or may be installed in the base 2. The air moving device 6 causes air 7 to move into the conduit 3 and much of the air to exit through opening 5. Orifices, openings or holes 9 of a specific pre-determined diameter are placed in the conduit 4 at a strategic point selected to direct the air 7 through the orifices 9 to an area near or at the critical spot or points 8 (including mercury spot or amalgam spot, which contains mercury) on the lamp 4.

In another embodiment, not shown, the opening 5 may be omitted allowing all the air 7 to be directed through the orifices 9. In yet another embodiment (not shown), a multitude of small conduits could be used to individually supply air 7 to orifices 9.

FIG. 3a shows a horizontal cross sectional view through the conduit 3. Air 7 flows through the orifices 9 and is directed to the critical spot 8 on the lamp 4. FIG. 3b shows a portion of the conduit 3 with the lamp 4. In FIG. 3c, the lamp 4 is removed to better show one of the orifices 9.

An alternate embodiment of this invention is shown in FIG. 4a which shows a portion of the conduit 3 with a diverter or nozzle 10 installed in the conduit 3 to improve air flow to the critical spot 8. The nozzle/diverter 10 contains the proper size orifice 9. FIG. 4b shows a view of the nozzle/diverter 10 from inside the conduit. An alternate embodiment for delivering cooling air 7 to the critical spot 8 is shown in FIG. 4c and it consists of one or more individual conduits 20 for each critical spot 8.

Figure 5:
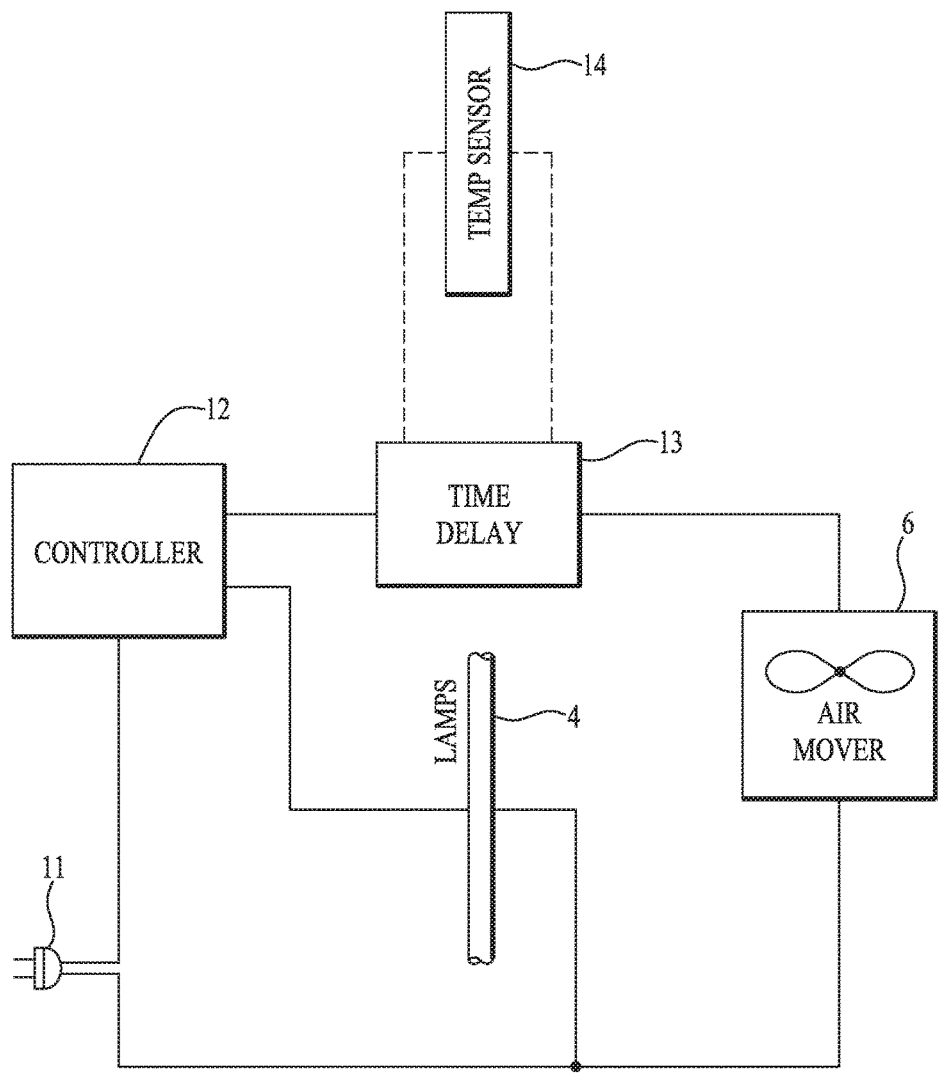
FIG. 5. A schematic showing a control circuit for controlling operation of the air moving component.
Figure 9:
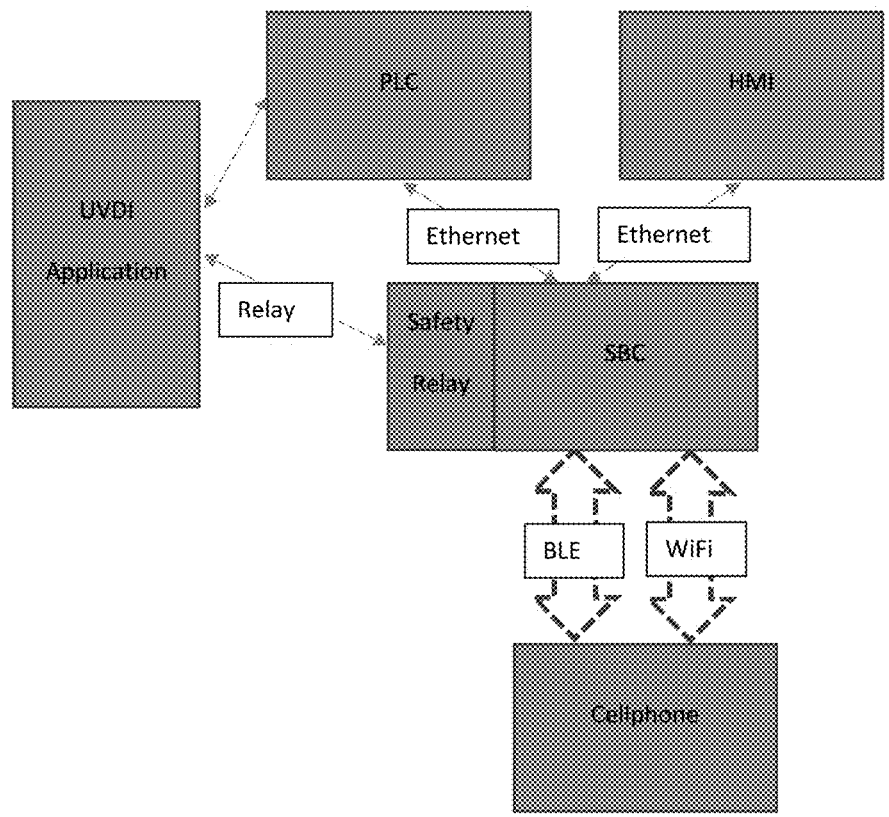
FIG. 9. An overview of the architecture of the PLC and BLE improvement.
Figure 10:
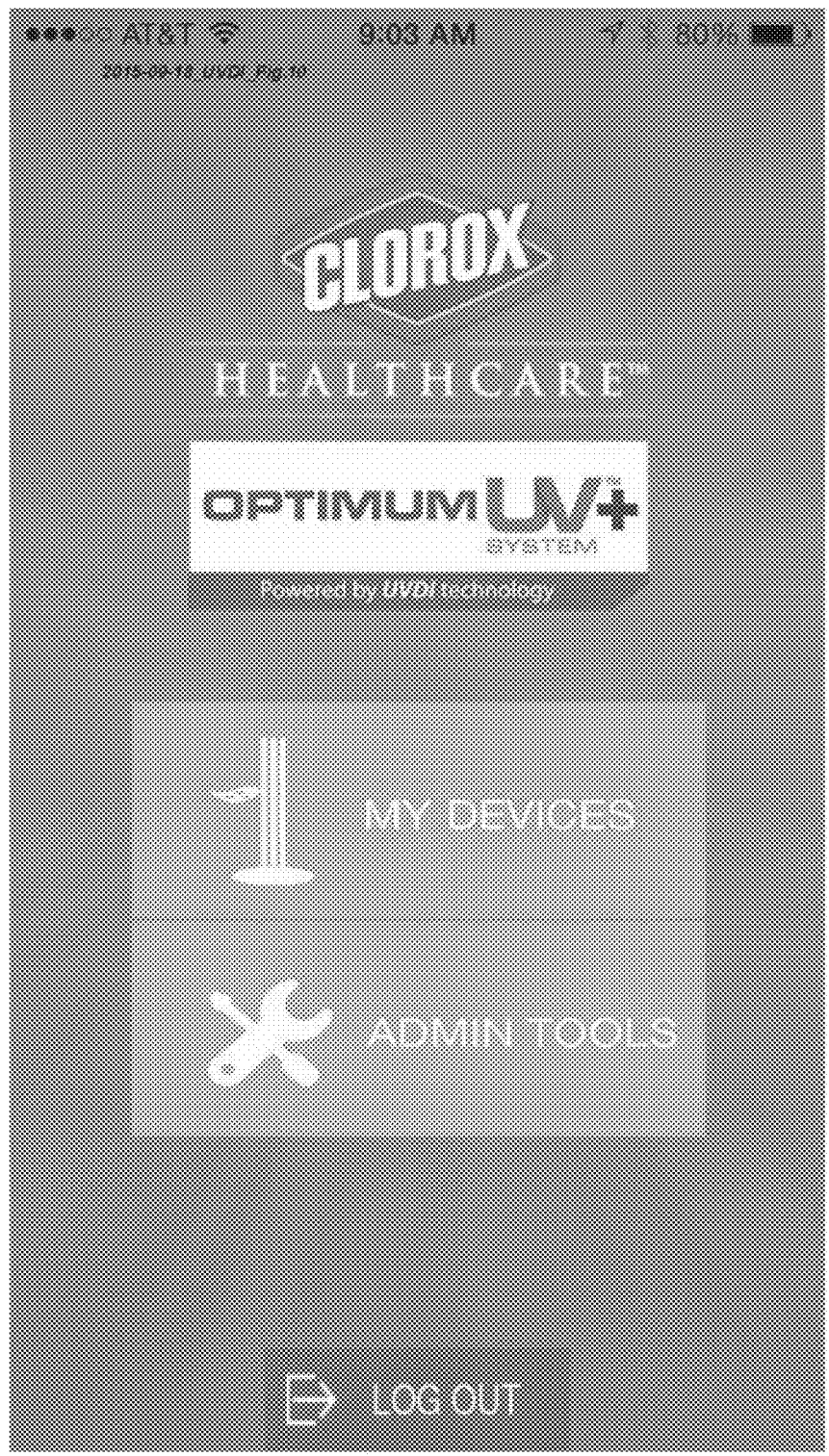
FIGS. 10-21 are screen shots from one embodiment of the invention (PLC & BLE improvement) as shown on the screen of a mobile computing device or Smart Phone.
Figure 11:
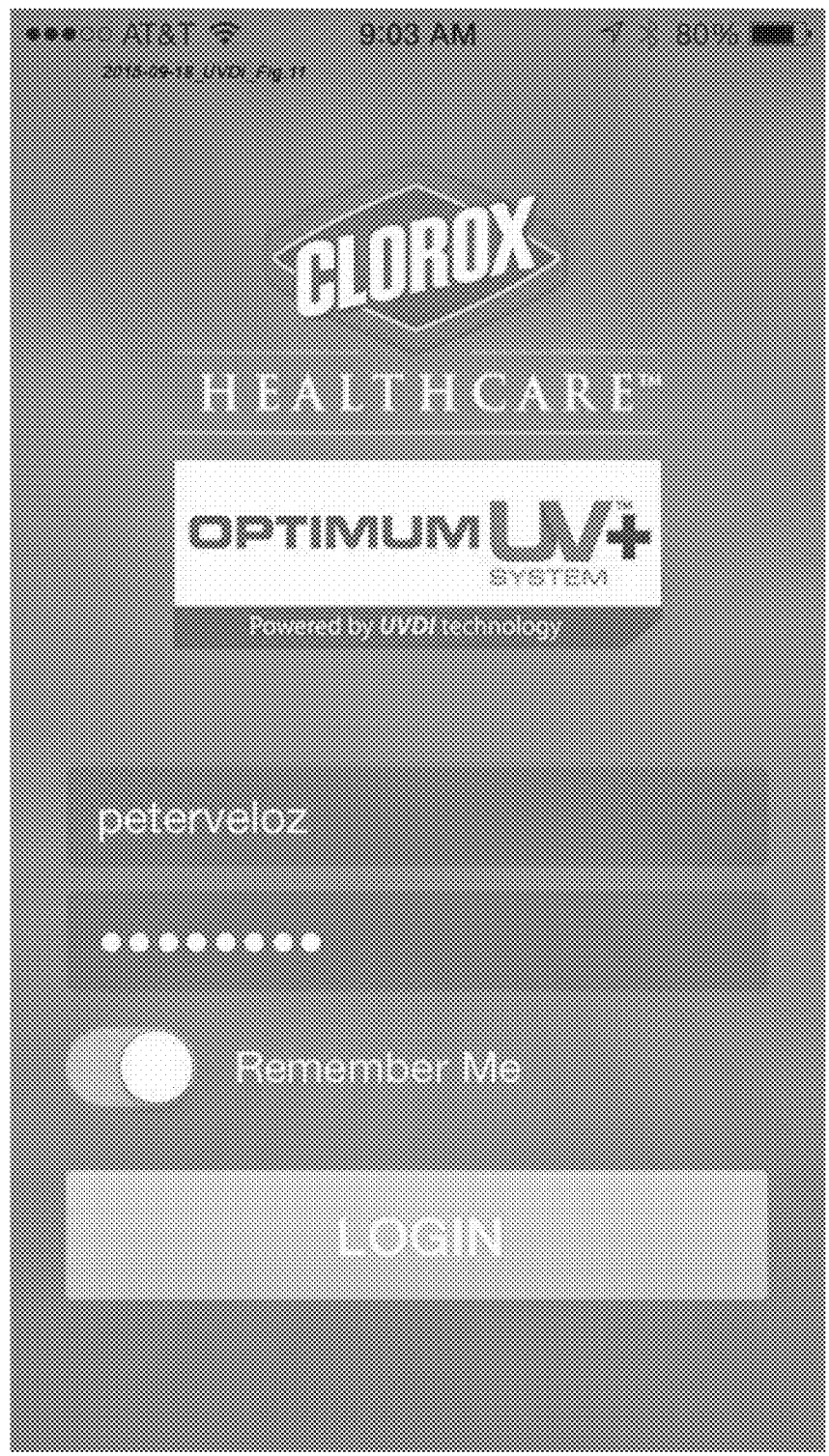
Figure 12:
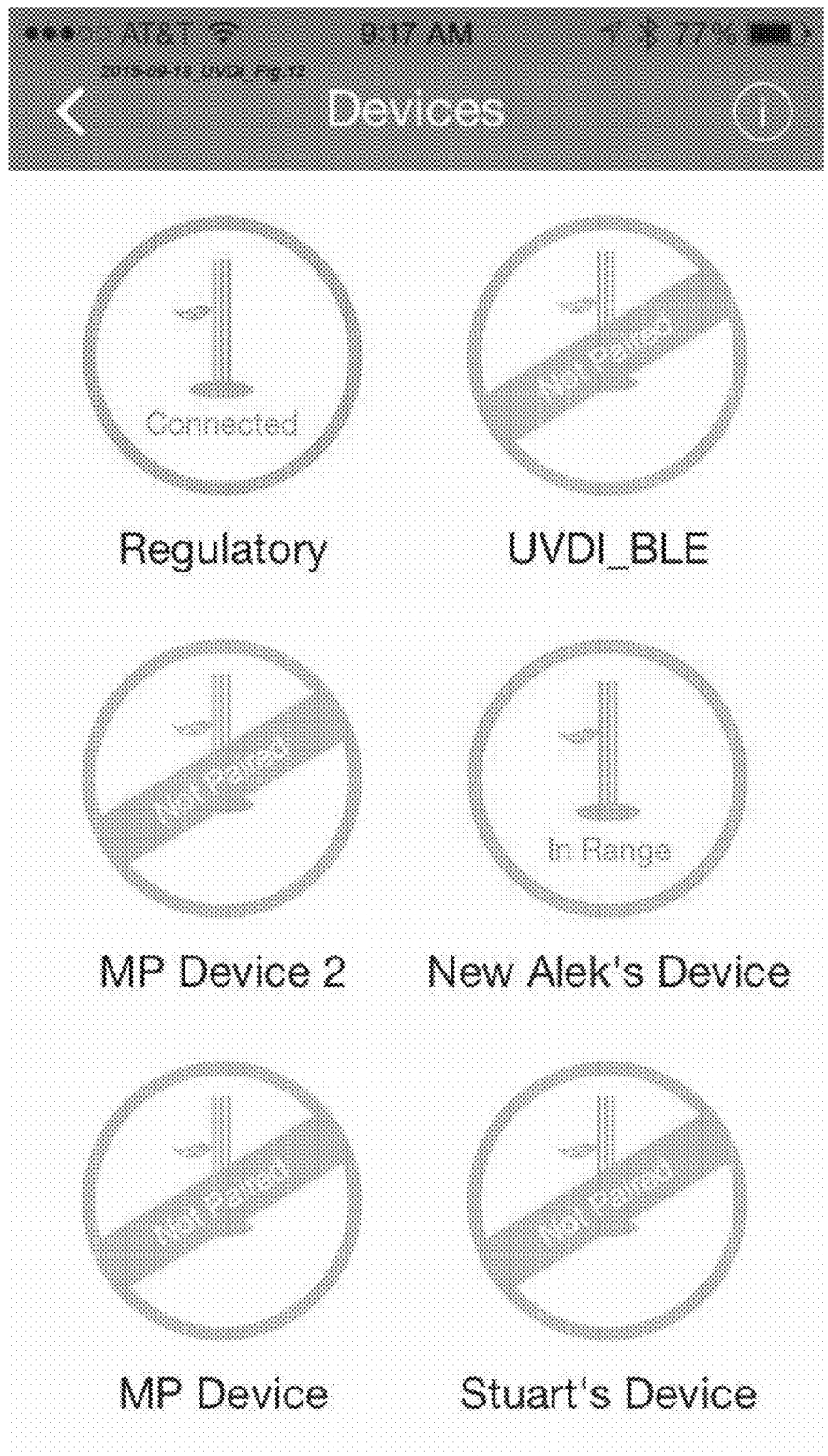
Figure 13:
Figure 14:
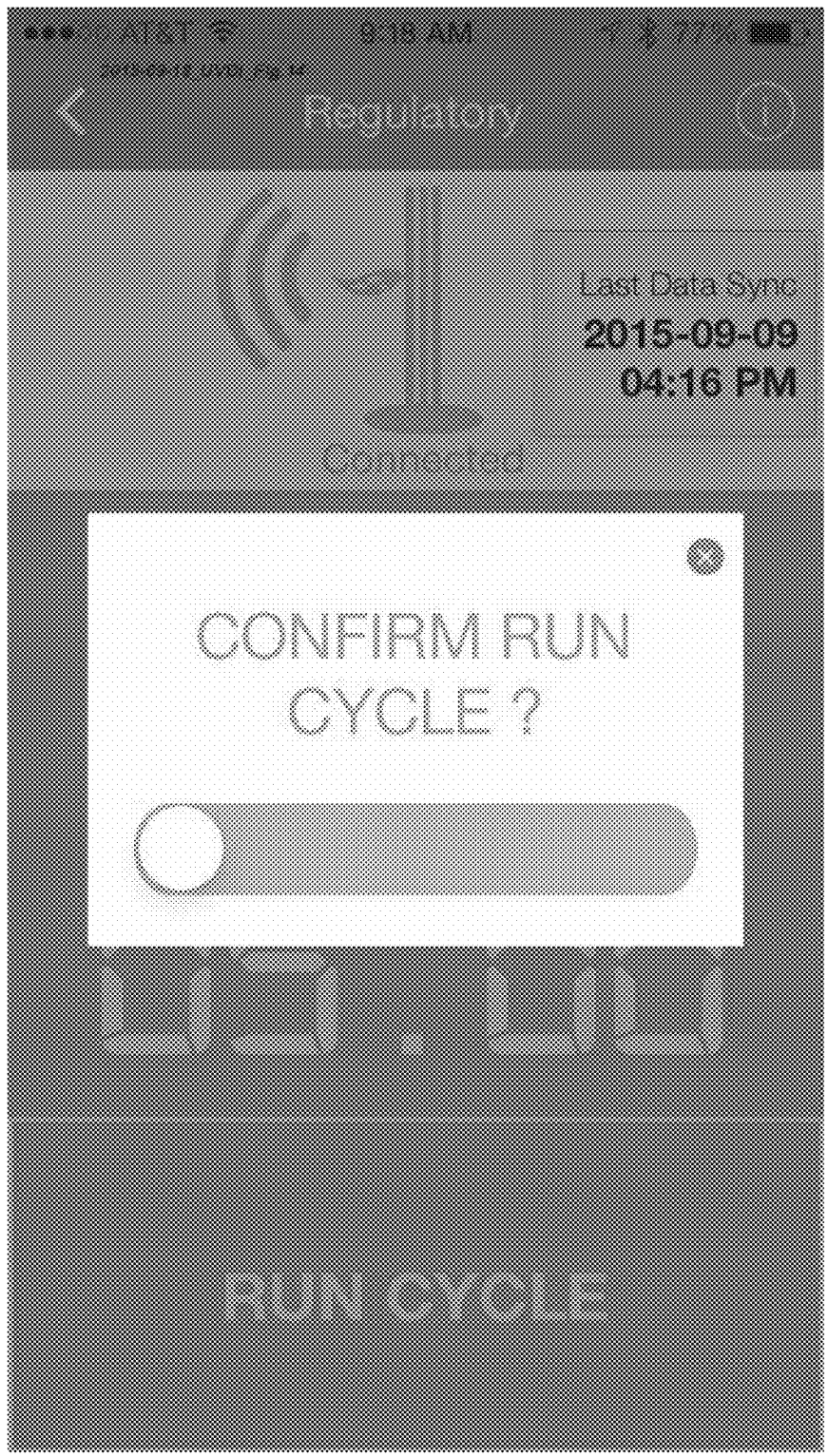
Figure 15:
Figure 16:
Figure 17:
Figure 18:
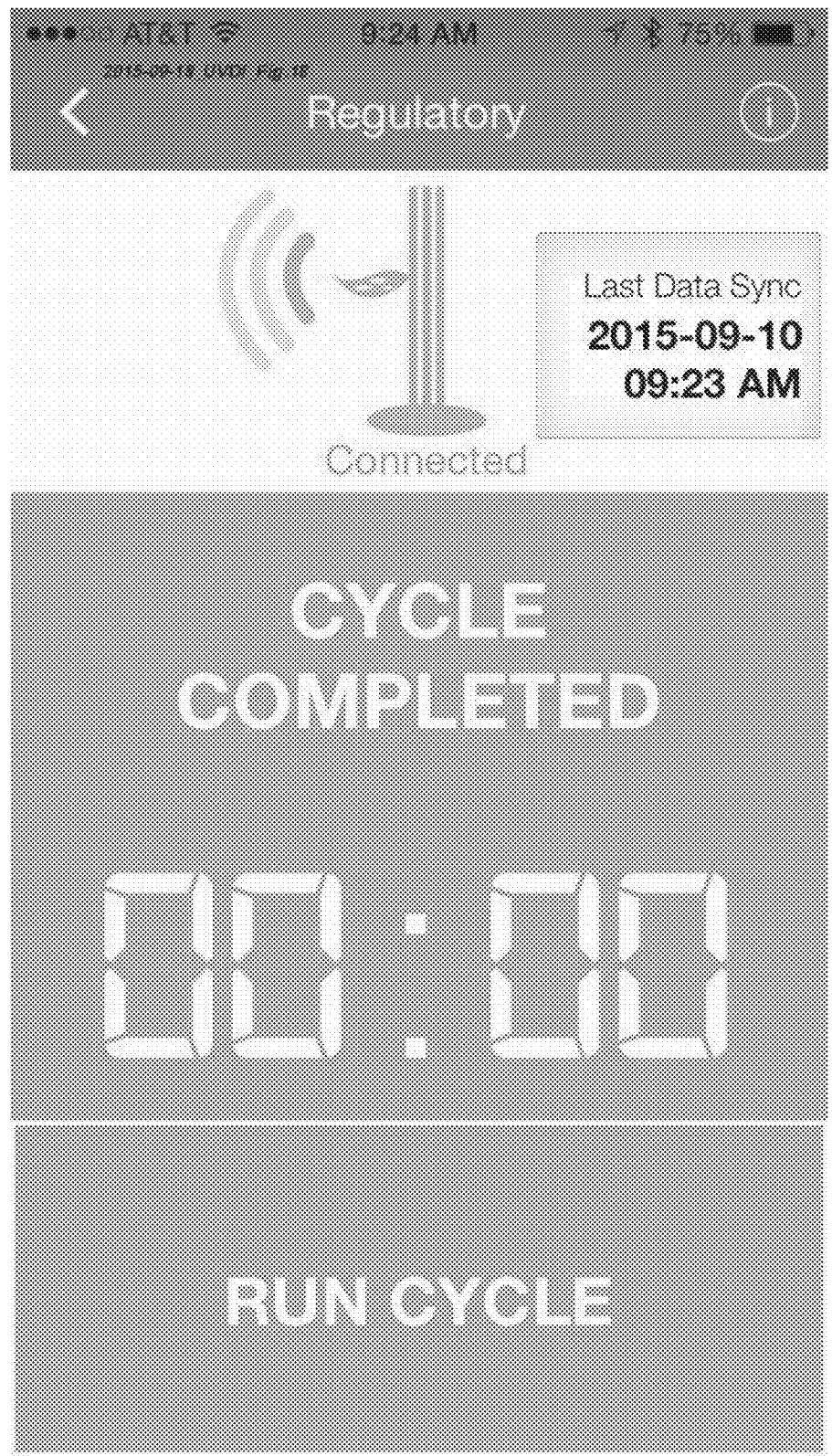
Figure 19:
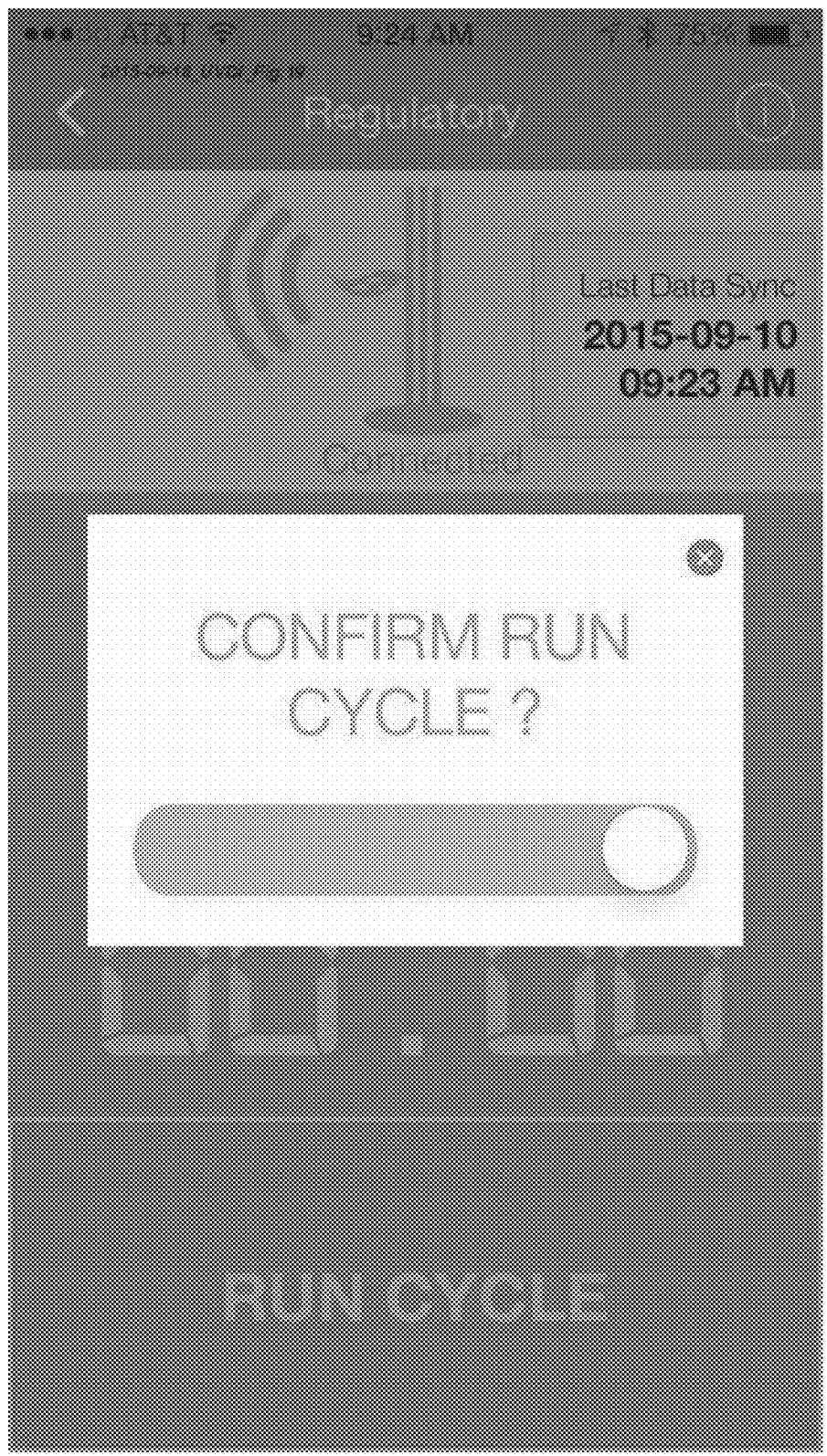
Figure 20:
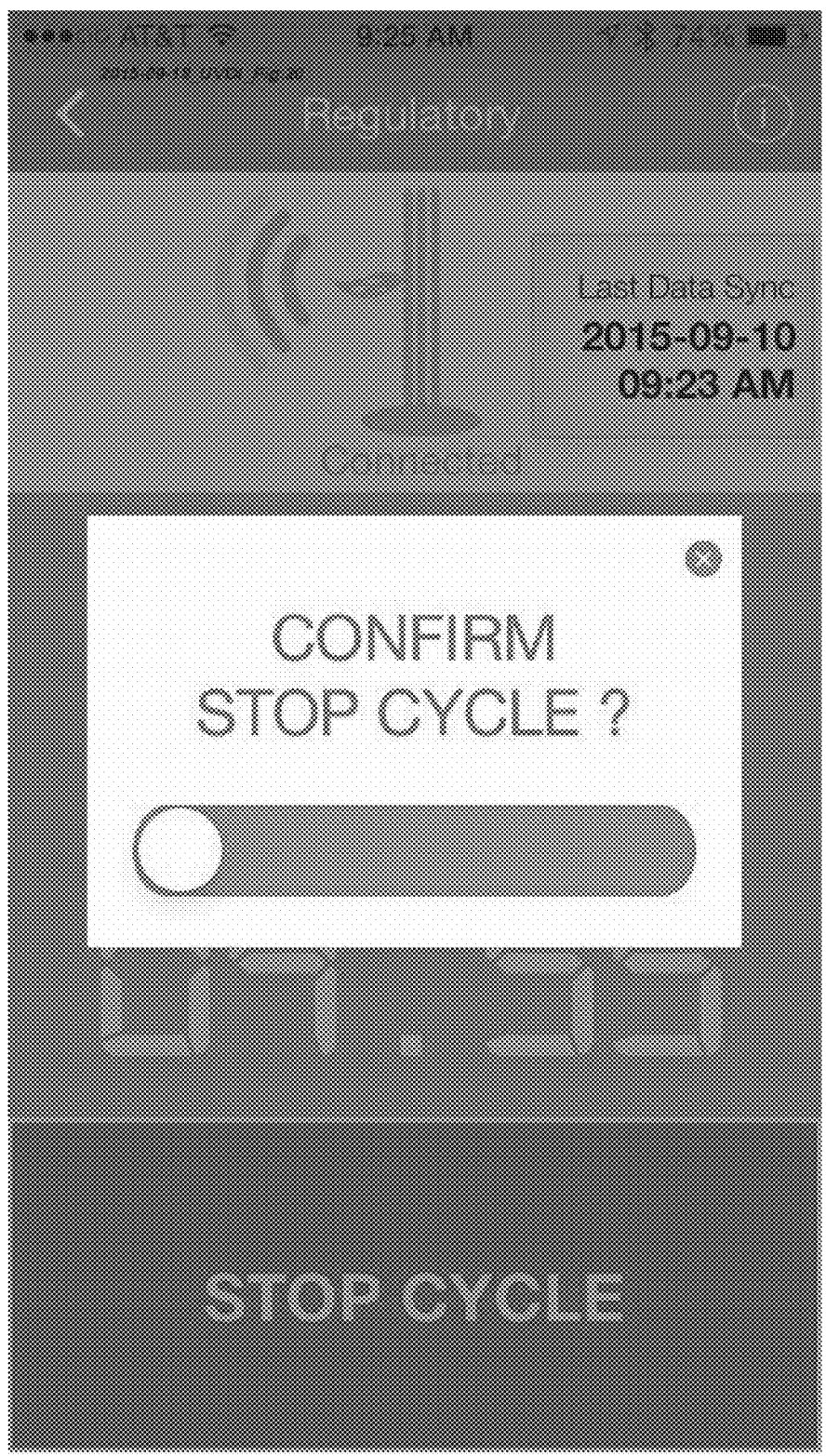
Figure 21:

Often, it is advantageous to allow the lamp to come up to the proper temperature rapidly prior to applying cooling air 7. A means (a part of this invention) is shown to delay operation of the air moving device 6 is shown in FIG. 5; a delay operation is useful to allow the UV lamp to reach a preferred operating temperature. Alternatively, this may also power a thermo electric cooling device 17. A source of power 11 powers a main controller 12, which normally operates the lamps 4 and the air mover 6, as appropriate. A hardware or software time delay 13 is located in the control circuit, such that operation of the air mover 6 can be controlled or delayed. Optionally, a temperature sensor 14 may be added to the time delay 13 or controller 12 to control operation of the air mover 6.

Alternate methods (another part of this invention) to remove heat from the critical spots 8 of the lamp 4 are shown in FIGS. 6 and 7. A heat sink collar 15 may be applied to the lamp 4 around the critical spot 8. Heat is transferred from the critical spot 8 to the ambient air. The heat sink 15 may or may not be additionally cooled with air from the orifices 9. In another embodiment, the heat sink 16 is larger and contacts a support 19 in the apparatus to further draw heat from the critical spot 8.

In yet another embodiment of the invention, shown in FIG. 8, a thermoelectric cooling/heating device 17 is used to control the temperature of the critical spots 8. The temperature of the thermoelectric heating/cooling device 17 and the heat controlling capacity may be controlled by a controller 18.

PLC & BLE:

UVDI's V-360 and V-360 Plus portable UV disinfection sanitizer product family employ a PLC (programmable logic controller) to control its operation and has a HMI (human machine interface) on the device for its user interface. One embodiment of using the invention includes: moving the UV device to a room, manually entering a specific time for a disinfection cycle on the HMI and leaving the room (to prevent exposure from UV radiation) until the cycle is complete. Motion sensors on the device prevent operation if people are present or enter the room during a cycle. The UV device is then moved to another location, and the process repeated. The device captures data such as date and time of operation, user name, room number, disinfection time, performance status etc. This data is currently stored on the PLC/HMI system locally and can be downloaded through a cabled connection to a supplied tablet that is provided with the UV device.

UVDI is currently working on the next generation of the device and plans to include some additional features, including without limitation: wireless connectivity to/from the UV Disinfection Device. This invention presents one preferred embodiment of the hardware and firmware solution that can be integrated with the PCL/HMI system on the UV device in order to communicate with the UV device wirelessly and transmit the data file to a UVDI controlled Cloud based server.

The main problem with existing PCL/HMI systems is that there was no way to communicate between a PLC using a wireless technology like BLE or Bluetooth Low Energy. BLE is preferred since most existing smartphones and other mobile computing devices have a built-in capability to communicate using small packets of encrypted data via BLE. To resolve this problem of communication between the mobile computing device (i.e. table or smartphone) and the UV device's PLC, there is presented a hardware and software module on the UV device, which allows access to the operating status of the device and the transfer of data (typically a .csv file) for further processing. Wireless connectivity is to be provided via BLE. Via BLE, the data should be able to be transmitted to a smart device (tablet or phone), which is enabled by a software application or mobile app. This app will serve as a gateway to view and move the data file to a Cloud based server from the smart device.

Additional connectivity can be provided through traditional wireless means such as WiFi or Bluetooth, but WiFi is generally crowded in a hospital or healthcare setting and also poses additional security complications; Bluetooth is range limited and requires too much energy. Looking at FIG.

9, the UV device employs the PLC with BLE to be able to communicate with the user's smartphone or tablet.

The single board computer can have multiple digital inputs for cycle monitoring and at least one digital output for the master shut-off. The BLE module/single board computer can have additional analog outputs to enable BLE connectivity of remote sensors to the PLC/HMI.

There is also connectivity for remote UV sensors, including without limitation: a wireless UV-C sensor. For example, this sensor can be placed at certain locations in the hospital room in close proximity to the UV device and will read the device output at that location. Through the BLE connection, the sensor is enabled and allows the sensor reading to be sent wirelessly (BLE) to the smart device such as tablet or phone, which is located outside the room, either though the single board computer or directly to the smart device. Sending the sensor information to the single board computer will provide the device the necessary input for determining the appropriate disinfection cycle time. It will also provide the user useful data to determine the appropriate placement of the device in the room as well as the appropriate cycle time.

Connectivity can also be established for room identification sensors. Specific room number identification can be programmed into a BLE beacon placed in the room. Through the BLE connection, the room information from the beacon is sent wirelessly to the PLC/HMI via the single board computer to record the room information. This functionality will eliminate the need for the user to enter the room number. Alternatively, the BLE beacons can transmit the room information directly to the smart device outside the room using the BLE connectivity.

There are warning signs and signals to provide visual or auditory indicators of the status of a disinfection cycle into the protective case (cover) for the device. The protective case can serve as the warning sign to prevent people from entering the room when the device is in operation. A visual indicator outside the room would let people know whether the disinfection cycle has been completed and when it is safe to go back inside the room and retrieve the UV device. The visual indicator can alternatively be integrated into a warning sign or device protective case placed outside the room when the disinfection cycle is in progress in the room. A smart device such as a smartphone, tablet or IPod Touch can be installed on the protective case or warning sign and serves as a visual indication of the status of a disinfection cycle. The smart device receives status of the disinfection cycle from the device via the BLE connectivity developed above; additionally, the BLE connectivity allows the smart device to receive data from the UV device.

Alternatively, the protective case or warning sign can house a BLE module instead of the smart device. This module has the connectivity, necessary processor strength and necessary I/Os. Alternatively, the BLE module (interface) can be free-standing or mountable outside the room. The module can have multiple outputs for the lights that will be triggered and at least one input for the master shut off button. The module can communicate with the PLC/HMI of the device and is easy to interpret. The module can have up to three light indicators to indicate the cycle status (e.g. red: cycle is on; yellow: cycle interrupted; green: cycle complete).

A robust battery power supply is to be provided that can last upwards of 1-3 years and be exchanged easily.

This invention also provides a remote cut off functionality, which will cut-off all power to the UV device via radio frequency or BLE, bypassing the PLC. This would serve as a master shut off of the UV system as a safety precaution, if needed.

The smart device or BLE module communicates to the PLC through a single board computer (SBC). The SBC is connected through hardwire to the PLC and HMI using the Ethernet port on the PLC. The SBC may also communicate with a wireless router or another internet connected device.

The single board computer (SBC) communicates with the PLC and HMI on a regular basis to establish the current status of the PLC and HMI, using commands specific to the PLC and HMI. This communication may also happen in response to a specific request from the smart device. This status and/or associated data is converted to a standard format by the SBC.

The mobile computing device or smart device may from time to time connect to the SBC using BLE in response to user requests. The SBC can convert these into requests to the HMI and/or PLC to initiate requested actions or to return logged data or status.

The inventors believe that the novel and non-obvious portions of this invention include:
1. Bluetooth or Bluetooth Low Energy control of PLC/HMI from Phone app;
2. Standardised BLE interface to PLC/HMI via translation layer [commands in JSON actioned via proprietary HMI/PLC commands]; in addition, it is possible to swap out to other HMI/PLC and keep the app the same;
3. BLE to Ethernet via translation layer;
4. Timer synchronization (i.e. free running timer on app).
5. Ability for the SBC to receive and record information from remote sensors (BLE beacons) and upload to PLC and HMI.

Wireless Connectivity to/from the UV Disinfection Device

The improvement to the above invention involves appropriate hardware & firmware solution that can be integrated with the PLC (programmable logic controller) and HMI system (human machine interface) on the device in order to communicate with the UV device wirelessly and transmit the data to a UVDI controlled Cloud based server. The hardware and software module presented enables access to the operating status of the UV device and the transfer of data (typically, a .csv file) for further processing. A computer system with a human machine interface can also be used.

Wireless connectivity is to be provided preferably via BLE (Bluetooth Low Energy) or another low energy wireless communication system. The data should be able to be transmitted via BLE to a smart device (tablet or smartphone) enabled by a mobile software application ("app"). This app will serve as a gateway to view and move the data file to a Cloud based server from the smart device.

Additional connectivity can be provided through WiFi. Different from the purpose to provide data transmission, this WiFi connectivity can provide the factory access to the device remotely on a scheduled and less frequent basis. The goal is for some diagnostic information to be gained by the factory and maintenance in the form of uploading necessary patches or updates to the PLC/HMI to be able to occur.

This invention improvement presents one preferred embodiment of a module with appropriate hardware and firmware that will provide both BLE and WiFi connectivity to the PLC as well as the HMI. Without being limiting, one preferred method of connection to the PLC/HMI is via the Ethernet port on the UV device.

This invention can employ a single board computer (SBC) that has Ethernet, Bluetooth LE, and Wi-Fi interfaces. The board can support a web browser to accept the web server page provided by the IDEC PLC model FC5A-D12K1E and HMI display model HG2G-5FT22TF-B (examples only and not intended to be limiting).

The single board computer in the device can be available as an IP-connected node on the Wi-Fi network to which it is connected. Data can be accessed at other locations subject to appropriate set up of firewalls, access control etc. within the network to which it attaches. The network setup can regulate access and can vary due to the location or environment; information should be encrypted.

Any connected device will be able to display the web page from the PLC and HMI over the Wi-Fi interface.

A smartphone or other wireless computing device can display the web page from the HMI display over the Bluetooth LE interface, and will display the web page from the PLC and HMI over the Wi-Fi interface. It is not necessary for both web pages to be accessed at the same time.

The firmware allows the operator to switch the wireless connectivity from BLE transmission to Wi-Fi. The PLC will have a digital output that can be connected to a digital input on the single board computer to turn the Wi-Fi: on and off.

Data download: the HMI can log event data internally, which can be periodically downloaded through a Bluetooth LE connected device, such as a smart phone. For example, the PLC manufacturer (IDEC) provides Windows software called "Data Downloader," which can download this data into a PC; there can also be an application that can download this data to the single board computer and make it available to Bluetooth LE connected devices.

Connectivity (I/O) for cycle status notification: the single board computer can have multiple or 3 digital inputs to provide the status of the UV Device and 1 digital output for the shut-off switch. This information should be retrievable by the smart device through BLE interface. This should include the necessary firmware to enable this connectivity.

Connectivity for remote sensors: the BLE module/single board computer should have multiple additional analog outputs to enable BLE connectivity of remote sensors.

One preferred and non-limiting example of the System Architecture includes: the central processor in the system is a single board computer (SBC) from Technologic Systems (TS-7680). Specific to this task, the SBC is equipped with: 2×network ports; 1×USB host port; 2×relay outputs; Flexible PSU; Integrated WiFi/BLE module; and Optional external BLE antenna.

The SBC is connected to the HMI and PLC, which comprise the UVDI system using Ethernet. It communicates with the HMI and PLC over Ethernet.

Certain information described below is presented out to a mobile computing device, such as a tablet or a Smartphone over the BLE interface. In addition, the SBC may revert to a WiFi connection for the transfer of data. A relay on the SBC controls the "emergency stop" to the UVDI application and may be viewed as a safety relay.

Communication with the PLC and HMI is achieved over the Ethernet interfaces using protocols, which are specific to the IDEC PLC and HMI's used. Internal registers, motor settings can be read/written to in order to determine the state of the system. In addition, log files may be recovered from the HMI in CSV format, again subject to the IDEC proprietary protocols.

At the simplest level, the cellphone will connect to the SBC using BLE. The SBC will advertise a GATT service and this will facilitate two way communication using a "serial line" type methodology.

In one preferred embodiment, the SBC will be commanded to open a WiFi line—either to the cellphone or to another service. This may be used to provide a maintenance channel to the SBC/HMI.

In this mode, the SBC will allow: (1) Direct communication to the PLC and HMI (as a gateway), enabling the use of standard IDEC tools; (2) Command to be given to upload log files directly to UVDI servers.

Communication between the smart phone and the SBC, over GATT (GATT is an acronym for the Generic Attribute Profile and defines the way that two Bluetooth LE devices transfer data back and forth using concepts called Services and Characteristics), can be in JSON format. This allows for flexibility and future expansion.

Possible Commands: Start Cycle; Stop Cycle; Emergency Stop; Return Cycle status; Return Cycle data; Countdown timer; Cycle time timer; Lamp status and alerts; and Room information.

One Possible Embodiment

Each transaction can be initiated from the cellphone and takes the following format:
{
  "Transaction ID": 1,
  "Command": "command"
}
Transaction ID is a monotonically increasing number. If the SBC receives a number that is out of sequence an error is reported and the application halts. "command" is per the command list below, and additional data may be included. Each transaction is responded to by the SBC, either as an acknowledgement or including the requested data, in the following format:
{
  "Transaction ID": 1
  "Response": "response"
}
Response is one of:
"OK"—acknowledgement of action.
"Error"—error occurred. An additional field "Error number": describes the error number (TBD) and "Error text": describes the error in textual format. Note that a non-sequential transaction ID is an error.
Commands are:
"Start Cycle"—start a treatment cycle.
"Stop Cycle"—stop a treatment cycle
"Emergency Stop"—open the safety relay
"Cycle status"—return the status of a cycle. Data returned from the SBC is:
  "Status": "Running"
  "Status": "Interrupted"
  "Status": "Complete"
"Cycle Data"—return cycle data. Note that this is a CSV file which is not specifically converted to JSON objects—but it is embedded within an array. Newline characters are escaped and treated as special characters to ease conversion.
Data returned is (in simplified form)
  "Data": ["Room", "Date", "In", "1001", "12/13/2015", "In", "1002", "12/14/2015"]
JSON can be defined as JavaScript Object Notation and is an open standard format that uses human-readable text to transmit data objects consisting of attribute-value pairs.
Bluetooth Low Energy (BLE):
From the webpage: http://www.bluetooth.com/Pages/low-energy-tech-info.aspx, which is incorporated by reference.

"The Low Energy Technology Behind Bluetooth Smart
Thanks to its innovative design, Bluetooth® Smart technology consumes only a fraction of the power of Classic Bluetooth radios. Bluetooth Smart extends the use of Bluetooth wireless technology to devices that are powered by small, coin-cell batteries such as watches and toys. Other devices such as sports & fitness, health care, keyboards and mice, beacons, wearables and entertainment devices are enhanced by this version of the technology. In many cases, it makes it possible to operate these devices for more than a year without recharging.

As with previous versions of the specification, the range of the radio may be optimized according to application. The majority of Bluetooth devices on the market today include the basic 30 foot, or 10 meter, range of the Classic Bluetooth radio, but there is no limit imposed by the Specification. With Bluetooth Smart, manufacturers may choose to optimize range to 200 feet and beyond, particularly for in-home sensor applications where longer range is a necessity.

Bluetooth Smart features provides:
  Ultra-low peak, average and idle mode power consumption
  Ability to run for years on standard coin-cell batteries
  Lower implementation costs
  Multi-vendor interoperability
  Enhanced range This enhancement to the Bluetooth Core Specification allows two types of implementation, dual-mode and single-mode. In a dual-mode implementation, Bluetooth low energy functionality is integrated into an existing Classic Bluetooth controller. The resulting architecture shares much of Classic Bluetooth technology's existing radio and functionality resulting in a minimal cost increase compared to Classic Bluetooth technology. Additionally, manufacturers can use current Classic Bluetooth technology (Bluetooth v2.1+EDR or Bluetooth v3.0+HS) chips with the new low energy stack, enhancing the development of Classic Bluetooth enabled devices with new capabilities.

Single-mode chips, which will enable highly integrated and compact devices, will feature a lightweight Link Layer providing ultra-low power idle mode operation, simple device discovery, and reliable point-to-multipoint data transfer with advanced power-save and secure encrypted connections at the lowest possible cost. The Link Layer in these controllers will enable Internet connected sensors to schedule Bluetooth low energy traffic between Bluetooth transmissions.

Registered members of the Bluetooth SIG can access in-depth technical information about Bluetooth low energy technology. (You must be on-line and logged in as a registered member of the SIG to access this link). If you're not a member, register today.

Technical Details
  Data Transfers—Bluetooth Smart (low energy) supports very short data packets (8 octet minimum up to 27 octets maximum) that are transferred at 1 Mbps. All connections use advanced sniff-sub rating to achieve ultra low duty cycles
  Frequency Hopping—Bluetooth Smart (low energy) uses the adaptive frequency hopping common to all versions of Bluetooth technology to minimize interference from other technologies in the 2.4 GHz ISM Band. Efficient multi-path benefits increase the link budgets and range
  Host Control—Bluetooth Smart (low energy) places a significant amount of intelligence in the controller, which allows the host to sleep for longer periods of time and be woken up by the controller only when the host needs to perform some action. This allows for the greatest current savings since the host is assumed to consume more power than the controller
  Latency—Bluetooth Smart (low energy) can support connection setup and data transfer as low as 3 ms, allowing an application to form a connection and then transfer authenticated data in few milliseconds for a short communication burst before quickly tearing down the connection
  Range—Increased modulation index provides a possible range for Bluetooth Smart (low energy) of over 100 meters
  Robustness—Bluetooth Smart (low energy) uses a strong 24 bit CRC on all packets ensuring the maximum robustness against interference
  Strong Security—Full AES-128 encryption using CCM to provide strong encryption and authentication of data packets
  Topology—Bluetooth Smart (low energy) uses a 32 bit access address on every packet for each slave, allowing billions of devices to be connected. The technology is optimized for one-to-one connections while allowing one-to-many connections using a star topology."

This invention refers to computing programs, applications or software, which are all synonymous and are used interchangeably. This invention can be applied to any computing device that is connected to a communication network or the Internet via wired or wireless connection.

The embodiments of the invention may be implemented by a processor-based computer system. The system includes a database for receiving and storing information from users and application software for users and displaying feedback information.

In accordance with the present invention, computer system operates to execute the functionality for server component. Computer system includes a processor and memory and disk storage. Memory stores computer program instructions and data. Processor executes the program instructions or software, and processes the data stored in memory. Disk storage stores data to be transferred to and from memory. Note that disk storage can be used to store data that is typically stored in the database.

All these elements are interconnected by one or more buses, which allow data to be intercommunicated between the elements. Note that memory is accessible by processor over a bus and includes: an operating system, a program partition and a data partition. The program partition stores and allows execution by processor of program instructions that implement the functions of each respective system described herein. The data partition is accessible by processor and stores data used during the execution of program instructions.

For purposes of this application, memory and disk are machine readable mediums and could include any medium capable of storing instructions adapted to be executed by a processor. Some examples of such media include, but are not limited to, read-only memory (ROM), random-access memory (RAM), programmable ROM, erasable programmable ROM, electronically erasable programmable ROM, dynamic RAM, magnetic disk (e.g., floppy disk and hard drive), optical disk (e.g., CD-ROM), optical fiber, electrical signals, light wave signals, radio-frequency (RF) signals and any other device or signal that can store digital information. In one embodiment, the instructions are stored on the medium in a compressed and/or encrypted format. As used herein, the phrase "adapted to be executed by a processor" is meant to encompass instructions stored in a compressed and/or encrypted format, as well as instructions that have to be compiled or installed by an installer before being executed by the processor. Further, system may contain various combinations of machine readable storage devices, which are accessible by processor and which are capable of storing a combination of computer program instructions and data.

A computer system also includes a network interface. Network interface may be any suitable means for controlling communication signals between network devices using a desired set of communications protocols, services and operating procedures. Communication protocols are layered, which is also referred to as a protocol stack, as represented by operating system, a CBE-communication layer, and a Transport Control Protocol/Internet Protocol (TCP/IP) layer. Network interface may also include connectors for connecting interface with a suitable communications medium. Those skilled in the art will understand that network interface may receive communication signals over any suitable medium such as twisted-pair wire, co-axial cable, fiber optics, radio-frequencies, and so forth.

A typical computer system includes a processor, a memory, disk storage, a network interface, and a protocol stack having a CBE-communication layer and a TCP/IP layer. These elements operate in a manner similar to the corresponding elements for computer system.

An apparatus for disinfection of air and surfaces, comprising: a UV lamp having a mercury amalgam spot or mercury spot; a power source; a conduit body, which has at least one hole that is located near the mercury amalgam spot of the UV lamp; and an air moving device, which delivers air through the conduit body in a first direction; and the at least one hole directs the air in a second direction and near the mercury spot of the UV lamp.

The apparatus can further comprise a computer system with a human machine interface (HMI); a wireless communication controller communicates to the computer system; whereby the air moving device provides cooling to alter the temperature near the mercury amalgam spot of the UV lamp, and the wireless communication controller controls the apparatus.

The computer system further comprises a programmable logic controller (PLC) and a computing device; the wireless communication controller can communicate to the programmable logic controller through the computing device; the computing device can be connected through hardwire to the programmable logic controller and the human machine interface using an Ethernet port on the programmable logic controller or a serial port or USB port or through a wireless router or an internet connected device.

The wireless communication controller can use Bluetooth Low Energy (BLE), low energy wireless communication or WiFi technology to communicate with the programmable logic controller; and the computing device of the apparatus has Ethernet, Bluetooth Low Energy and WiFi interfaces; the at least one remote UV sensors can be wirelessly connected to said apparatus and said wireless communication controller. The wireless communication controller can be a Smart Phone, a tablet, a handheld PC or a mobile computing device. The computing device of the apparatus communicates with the programmable logic controller and the human machine interface, and the computing device of the apparatus uses commands specific to the programmable logic controller and the human machine interface; the apparatus transmits data to an Internet based server; the wireless controller controls and displays the operating status of the UV apparatus; the computing device of the apparatus is a single board computer (SBC).

The apparatus can also use or employ a dose verification device having at least one coupon, the at least one coupon having a UV sensitive portion, which can undergo a color change, in response to a UVC dose corresponding to a UVC wavelength range from 200 nm to 280 nm; the at least one coupon has a UV dosage reference portion, which is calibrated to a certain UVC dose to achieve a level of disinfection for a target organism.

Title: Method and Apparatus for Real-Time Verification of UVC Disinfection Dose

Inventors: Richard Hayes, Thousand Oaks, Calif.; Ashish Mathur, Valencia, Calif.; Peter Veloz, Glendale, Calif.; David Witham, Ventura, Calif.; Mitch Babkes, Santa Clarita, Calif.; Aleksandr Shostak, Northridge, Calif.

This application claims the benefit of U.S. Provisional Patent Application No. 61/761,670, filed on Feb. 6, 2013, which is incorporated by reference in entirety.

The use of germicidal ultraviolet (UV-C or UVC) based devices to inactivate microorganisms such as bacteria, viruses and mold is well known. In recent years, UVC disinfection devices have gained considerable interest in hospitals to disinfect patient rooms, operating rooms and isolation wards. One of the primary causes of hospital acquired infections (HAI) is via cross contamination from "high-touch" surfaces in patient rooms, where conventional cleaning practice of using chemical disinfectants has been found to be inadequate. Several portable UVC disinfection devices have been introduced in hospitals and are used as an adjunct technology to conventional cleaning using chemical disinfectants.

UVC devices employ one or more lamps emitting a spectral wavelength output of approximately 254 nm which disrupts the DNA structure of the micro-organisms, rendering them harmless and unable to reproduce. There is considerable amount of literature enumerating the required UVC dose to inactive target micro-organisms. The dose applied by a UVC device is a function of lamp intensity delivered to the target surface over a certain time period as follows:

Dose applied (microwatts-s/cm$^2$)=Lamp intensity (microwatts/cm$^2$)×time (second)

For example, the dose required to achieve 99% disinfection of MRSA is approximately 10,000 microwatts-s/cm$^2$, whereas the dose required to achieve 99% disinfection of *Clostridium Difficile* (C-diff) spores is approximately 40,000 microwatts-s/cm$^2$. Therefore, if the lamp intensity is 100 microwatts/cm$^2$, it will take approximately 100 seconds to achieve 99% disinfection of MRSA and 400 seconds to achieve 99% disinfection of C-diff spores.

It is therefore highly desirable to have an accurate measurement of the dose applied by a UVC disinfection device on target surfaces or microorganisms. While several UVC disinfection devices have been introduced in healthcare settings, there is a lack of real time efficacy measurement of these devices. Some devices come with timers to turn on these devices for a predetermined amount of cycle time, and some devices measure reflected intensity to determine time period for a cycle.

UVC is a line of sight technology, and therefore, the dose on a target surface can be lower than expected if there is any obstruction in the path of the light, or if the region is shadowed. In such cases, determining the time required to deliver a specified dose to a target surface becomes extremely subjective and inaccurate. None of the UVC disinfection devices currently offered in these applications offer any means of verifying the actual dose on a target surface.

U.S. Pat. No. 6,475,433 McGeorge, which is incorporated by reference, presents a method and apparatus for verifying ultraviolet sterilization; however, this patent fails to disclose a method or apparatus to disinfect and to verify a certain level of disinfection in a room and on multiple surfaces, including "high touch" surfaces. See also U.S. Pat. No. 7,589,331 Havens; U.S. Pat. No. 8,334,521 Deshays. All publications, patents, and patent applications mentioned in this specification are herein incorporated by reference to the same extent as if each individual publication, patent, or patent application was specifically and individually indicated to be incorporated by reference.

Figure 25:
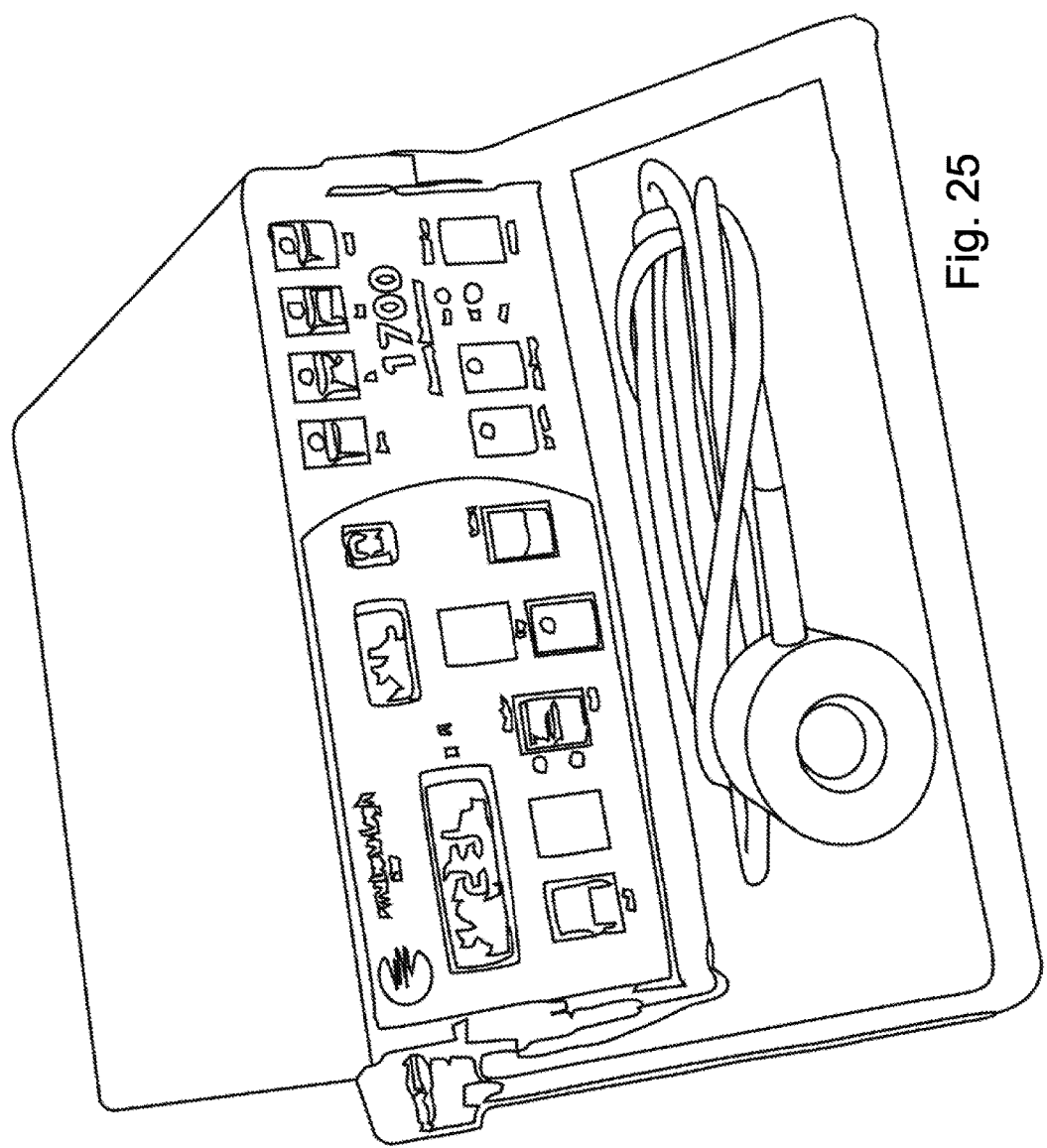
FIG. 25 shows a radiometer device.

Current best practices to measure UVC dose from a UVC lamp or disinfection device employ a radiometer. A sensor probe can be built into the radiometer or can be attached externally to the radiometer. An example of a typical radiometer with an external sensor probe is the ILT 1700 manufactured by International Light. See FIG. 25.

The radiometer has an electronic display which can display the intensity and/or dose read by the sensor. The radiometer can be configured to specific wavelengths between 200 nm to 1100 nm and can be calibrated to 254 nm for UVC wavelength. The UVC dose applied by a device is measured by placing the radiometer probe on the target surface facing the UVC device, turning on the UVC device and reading the intensity or cumulative dose applied on the display. One known limitation of the radiometer sensor probe is the narrow field of view of the probe. Depending on the type of radiometer used, the viewing angle of the sensor probe is limited and is typically only up to 120 degrees. As a result, the intensity or dose reading obtained is highly dependent on the angle of the sensor probe with respect to the UVC lamp or device.

The dose therefore applied on a target surface is subjective and depends on the orientation of the sensor probe with respect to the UVC lamp or device; as a result, the results obtained can be inaccurate and do not represent the actual dose applied by the UVC lamp or device on the target surface. The radiometer approach may be effective only in settings where the target surface is in direct line of sight of the radiometer sensor probe. Another limitation is that only one point can be measured at a time, unless multiple radiometers are used simultaneously.

Furthermore, the radiometer is bulky, expensive (over $5000) and impractical to implement in a hospital setting, as one would require multiple units in a patient room to measure applied doses at various locations in a patient room simultaneously.

From the preceding descriptions, it is apparent that the devices currently being used have significant disadvantages. Thus, important aspects of the technology used in the field of invention remain amenable to useful refinement.

It is the purpose of this invention to provide a method of verifying a level of disinfection applied by a UVC light generating device in a room having at least one high touch surface and using a dose verification device; the dose verification device having at least one coupon or multiple coupons; each said coupon having a UV sensitive portion, which can undergo a color change, in response to a UVC dose corresponding to a UVC wavelength range from 200 nm to 280 nm; said steps comprising:

1) Placing the at least one coupon on the at least one high touch surface in the room;
2) Activating the UVC light generating device;
3) Verifying the level of disinfection applied to the surfaces based on the color change of the coupon; and
(4) UVC light generating device is moved to a different location in the room; and repeating steps (1) through (3).

There is also presented a method of determining an optimal placement of and an exposure time for a UVC disinfection device, while using a dose verification device; the dose verification device having at least one coupon, but preferably multiple coupons including a first coupon and a second coupon; each said coupon can have a UV sensitive portion, which can undergo a color change, in response to a UVC dose corresponding to a UVC wavelength ranging from 200-280 nm; and each said coupon can have a UV dosage reference portion, which is calibrated to the UVC dose required to achieve a level of disinfection for an organism; said steps comprising:

1) Placing the first coupon on a first surface in the room;
2) Placing the second coupon on a second surface in the room;
3) Activating the UVC disinfection device at a first location;
4) Verifying the level of disinfection applied to the first surface and the second surface based on the color change on the first coupon and the second coupon in relation to the UV dosage reference portion; and
5) Moving the UVC disinfection device to a second location and repeating the steps (1) through (4).

The above methods can also have at least one coupon, which has a UV dosage reference portion, which is calibrated to a certain UVC dose to achieve different levels of disinfection for one or more target organisms; the at least one coupon can have an identification area for notation of essential user information.

This invention also presents an apparatus for verifying a level of disinfection applied by a UVC light generating device in a room having multiple surfaces or "high touch" surfaces comprising: a dose verification device having at least one coupon and preferably multiple coupons, such as a first coupon and a second coupon; each said coupon can have a UV sensitive portion, which can undergo a color change, in response to a UVC dose corresponding to a UVC wavelength range from 200 nm to 280 nm; and the first coupon is placed on a first surface in the room; the second coupon is placed on a second surface in the room; whereby after activating the UVC light generating device, one can verify the level of disinfection applied to the first surface and the second surface based on the color change on the first coupon and the second coupon; each said coupon can have a UV dosage reference portion, which is calibrated to a UVC dose required to achieve a first level of disinfection for a first organism or different levels of disinfection for multiple organisms.

The present invention introduces such refinements. In its preferred embodiments, the present invention has several aspects or facets that can be used independently, although they are preferably employed together to optimize their benefits. All of the foregoing operational principles and advantages of the present invention will be more fully appreciated upon consideration of the following detailed description, with reference to the appended drawings.

Figure 23:
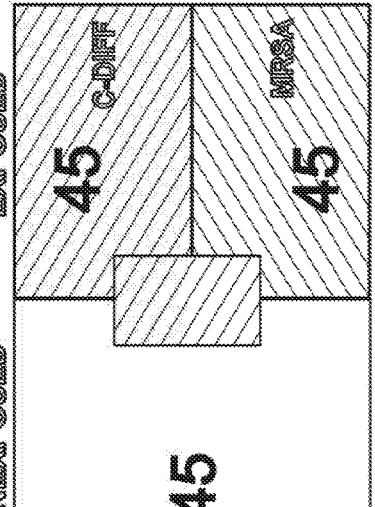
FIG. 23 shows the Dose Verification Card or coupon of FIG. 1 after exposure to UVC light; note how Part No. 40 has changed its appearance in relation to Part No. 45, C-Diff.
Figure 22:
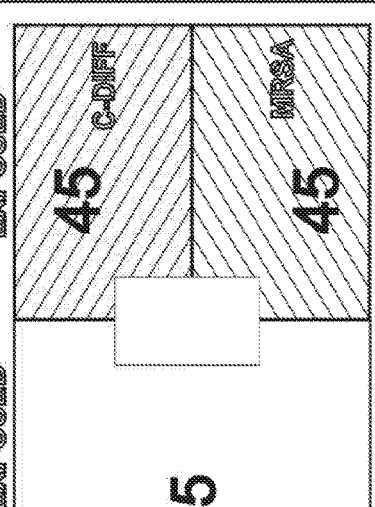
FIG. 22 shows one preferred embodiment of the invention, namely a Dose Verification Card or coupon; this embodiment can have the following areas on the card or coupon: an area for providing information about the patient, room and disinfection cycle; a UVC photo-chromic intensity indicator area; and a UVC reference area.
Figure 24:
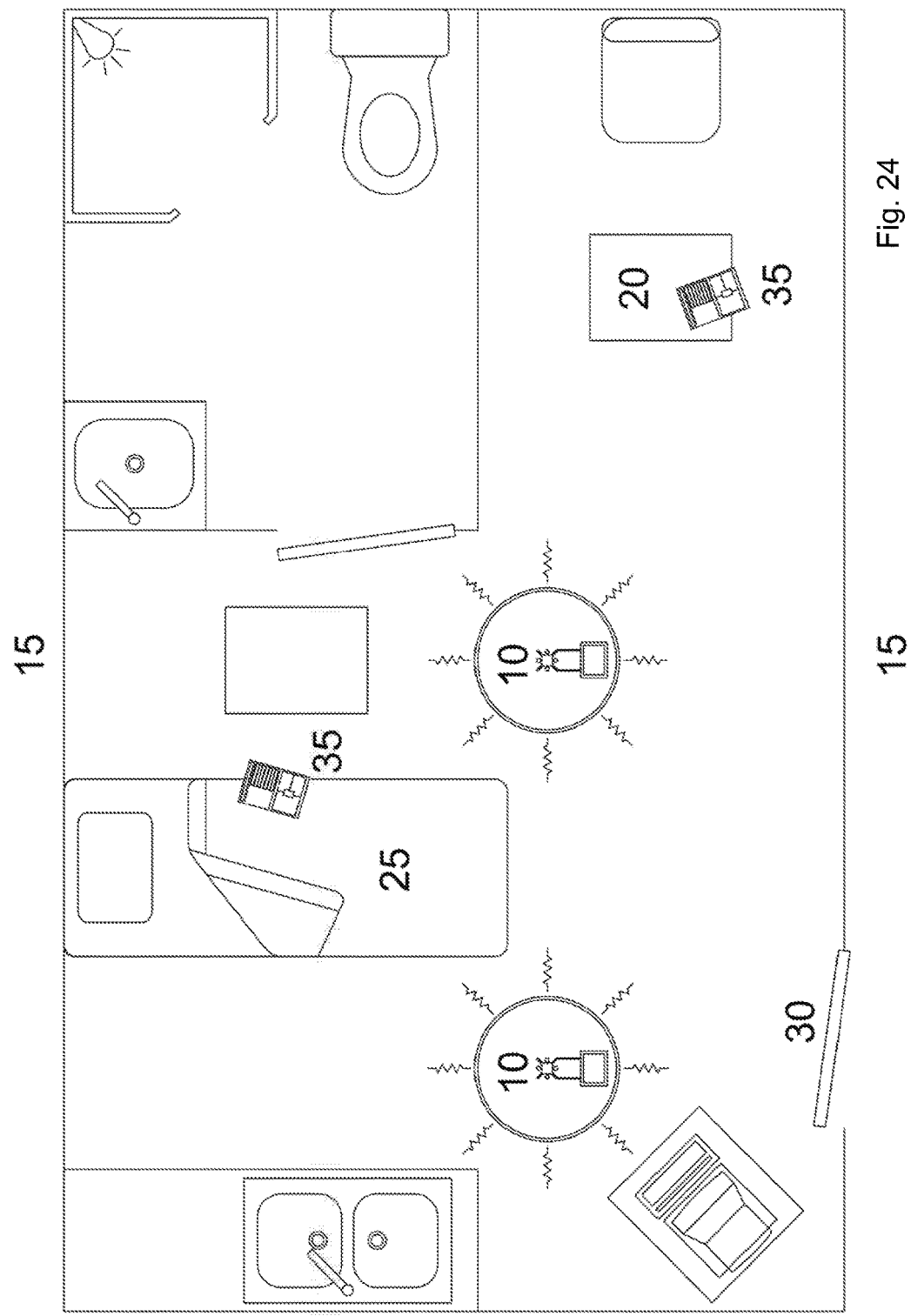
FIG. 24 shows a room schematic that shows one preferred embodiment of the method of disinfection and method of verifying disinfection and the apparatus to disinfect.

Detailed Description of the Dose Verify Apparatus:

This invention provides a novel approach to verify the disinfection dose applied by a UVC device that is relatively quick, reliable and inexpensive, as shown in FIG. 22-24.

This invention provides a dose verification card in conjunction with the UVC disinfection device to verify and record the applied dose by the UVC disinfection device at a target location. The use of this dose verification card solves the ambiguity regarding efficacy of the UVC disinfection device and allows the healthcare professional with a means to verify successful disinfection of target touch surfaces.

As shown in FIG. 22-24, in this approach, the applied UVC dose is verified through the use of photo-chromic intensity indicator labels provided with the device, which work on the principle of color change as a function of applied intensity or dose. These labels are specifically designed to be sensitive to UVC exposure; for example when exposed to UVC, the yellow labels undergo a gradual color change from yellow to green that is directly related to the UVC dose received.

One of the key advantages of these intensity labels over the radiometer sensor probe is that the label is two-dimensional and has a viewing angle of 180 degrees in all planes. Unlike the radiometer sensor probe, the intensity label is independent of its orientation with respect to the lamp and will therefore have an accurate measure of the dose applied on the surface on which the label is located. Furthermore, the labels are relatively inexpensive as compared to the radiometer probe and hence can be applied simultaneously at various locations in a patient room to verify the dose applied by the UVC disinfection device.

These UVC dose verification device or coupons can be placed in "high touch" areas and surfaces in the room to be disinfected, including without limitation: surfaces underneath chairs, tables and handles. These coupons can have adhesive backing or be attached via hook/loop attachments or holders with adhesive, hook/loop attachments, holes or hooks.

The use of photo-chromic or color change labels has been typically used to measure the degree of curing for UVA/UVB based inks. In curing applications, the adhesive backed label is placed on a sample product or substrate and processed to the proper cure rate. However, the use of such photo-chromic intensity labels to verify the dose applied by UVC disinfection devices in hospital settings is neither obvious nor straightforward. Different UVC disinfection devices use different wavelengths or a range of wavelengths. This invention requires these intensity labels to be calibrated for specific UVC wavelength corresponding to the UVC output of the UVC disinfection device, preferably corresponding to a wavelength ranging from 250 to 265 nm and more typically at approximately 254 nm.

Further, the UVC intensity labels have to be calibrated to provide a certain level of dosage for that environment. In one example, the UVC intensity labels can be configured to achieve dose levels corresponding to one log reduction (D90% disinfection), two log reduction (D99% disinfection), three log reduction (D99.9% disinfection) or greater of the micro-organism.

The dose verification card as shown in FIG. 22-24 comprises essential information regarding the hospital room, target location, date and time, operator name, etc. Each dose card has predetermined and calibrated color references for untreated (zero dose) and selected dose levels. In a preferred embodiment, one of the color references corresponds to a dose to achieve 99% disinfection MRSA, and a second color reference corresponding to a dose to achieve 99% disinfection of C-diff spores. In other embodiments, the color reference can correspond to a dose required to achieve 99% disinfection of any other microorganism bacteria, virus or mold. The dose verification also comprises an unexposed dose intensity label affixed to the center of the dose color references.

In a typical verification test, the operator will fill out the essential information on the dose verification cards or coupons and place the cards or coupons on the target surfaces, including "high touch" surfaces. The UV disinfection cycle is then performed for a predetermined period of time as per recommendations by the manufacturer. At the end of the cycle, the operator verifies whether the exposed dose intensity label is lighter or darker than the colored reference. If the exposed dose intensity label is lighter than the colored reference, the operator can increase the cycle time; or if the exposed dose intensity label is darker than the colored reference, the operator can choose to shorten the disinfection cycle time.

Alternatively, the operator can locate the UVC generating device at another location that will help achieve the desired dose to the target surfaces. In any event, the operator is able to ensure that the target surface has been disinfected successfully.

The scope of this invention is not limited to use for healthcare settings and can also be applied to other applications where UVC disinfection technology is used.

1) A method of verifying the dose applied by a UVC disinfection device on a target surface employing one or more dose verification cards to verify actual dose received at one or more target locations in a confined space, and upon determination of the dose delivered by the UVC disinfection device, adjusting the disinfection cycle time of the UVC disinfection device to achieve the desired dose whereby the dose verification card comprises: a photo-chromic UV dose intensity label, whereby the dose intensity label is calibrated to a UVC wavelength ranging from 250 to 265 nm and most preferably 254 nm; one or more colored reference matching the color of the dose intensity label corresponding to a specified dose or log reduction (0, D90, D99, D99.9, D99.99 . . . ).

2) A dose verification card to verify the dose applied by a UVC disinfection device comprising: a photo-chromic UV dose intensity label, whereby the dose intensity label is calibrated to a UVC wavelength ranging from 250 to 265 nm and most preferably 254 nm; And one or more colored reference matching the color of the dose intensity label corresponding to a specified dose or log reduction (0, D90, D99, D99.9, D99.99 . . . ).

Method of Verifying a Level of Disinfection Applied by a UVC Light Generating Device in a Room Having Multiple Surfaces:

As shown in FIG. 22-24, there is a method of verifying the level of disinfection applied by a UVC light generating device in a room having multiple surfaces and using a dose verification device.

The method can employ one coupon alone, but it is best to use at least two or multiple coupons located in different parts of the room and preferably in "high touch areas." High touch areas include without limitation: door handles; arm rests; tops and sides of chairs; call buttons; surfaces of tables, chairs and doors. In one preferred embodiment, the dose verification device uses a first coupon and a second coupon; each said coupon can have a UVC sensitive portion, which can undergo a color change in response to a UVC dose corresponding to a UVC wavelength range from 200 nm to 280 nm or another desired UVC range; and each said coupon can also have a UVC dosage reference portion, which is calibrated to a UVC dose required to achieve a first level of disinfection for a first organism or multiple organisms or bacteria.

The level of disinfection can be based on time or a percentage of eradication or elimination of said organism, such as 99% elimination rate. The method steps include:
1) Placing the first coupon on a first surface in the room;
2) Placing the second coupon on a second surface in the room;
3) Activating the UVC light generating device (for a set amount of time); and
4) Verifying the level of disinfection applied to the first and the second surfaces based on the color change on the first coupon and the second coupon in relation to the UVC dosage reference portion.

With this method, the UVC dosage reference portion of each said coupon can have another or second level of disinfection for the first organism; the UVC dosage reference portion of each said coupon can have a first level of disinfection for multiple organisms; each said coupon can have an identification area for notation of essential user information, such as name, time, date and room number; UVC light generating device can be moved to a different location in the room; and allows for repeating steps (1) through (4).

Method of Determining an Optimal Placement of and an Exposure Time for a UVC Disinfection Device, while Using a Dose Verification Device:

As shown in FIG. 22-24, this invention also presents a method of determining an optimal placement of and an exposure time for a UVC disinfection device, while using a dose verification device; the dose verification device can employ one coupon, but preferably uses multiple coupons, such as a first coupon and a second coupon; each said coupon can have a UV sensitive portion, which can undergo a color change, in response to a UVC dose corresponding to a UVC wavelength ranging from 200-280 nm or another desired UVC range; and each said coupon can have a UV dosage reference portion, which is calibrated to a UVC dose required to achieve a first level of disinfection for an organism.

The method has steps comprising:
1) Placing the first coupon on a first surface in the room;
2) Placing the second coupon on a second surface in the room;
3) Activating the UVC disinfection device at a first location;
4) Verifying the level of disinfection applied to the first and the second target surfaces based on the color change on the first coupon and the second coupon in relation to the UVC dosage reference portion; and
5) Moving the UVC disinfection device to a second location and repeating the steps (1) through (4).

With this method, the UVC dosage reference portion of each said coupon can have a first level of disinfection for multiple organisms; the UVC dosage reference portion of each said coupon can have more than one levels of disinfection for said multiple organisms.

Apparatus for Verifying a Level of Disinfection Applied by a UVC Light Generating Device in a Room Having Multiple Surfaces:

As shown in FIG. 22-24, there can also be an apparatus for verifying a level of disinfection applied by a UVC light generating device in a room having multiple surfaces comprising: a dose verification device having at least one coupon, but preferably use of multiple coupons, including without limitation a first coupon and a second coupon; each said coupon can have a UV sensitive portion, which can undergo a color change, in response to a UVC dose corresponding to a UVC wavelength range from 200 nm to 280 nm or another desired UVC range; and each said coupon can have a UVC dosage reference portion, which is calibrated to a UVC dose required to achieve a first level of disinfection for a first organism.

The apparatus is used by placing at least one coupon or preferably multiple coupons in different locations in the room to be sanitized; in one preferred embodiment, the first coupon is placed on a first surface in the room, and the second coupon is placed on a second surface in the room; whereby after activating the UVC light generating device, one can verify the level of disinfection applied to the first surface and the second surface based on the color change on the first coupon and the second coupon in relation to the UV dosage reference portion. This apparatus can be used again to verify and maximize the disinfection in a particular room or space.

An example of a UVC light apparatus is the V-360+ Room Sanitizer device from UltraViolet Devices, Inc. of Valencia, Calif. and U.S. Design Pat. No. D684671, which is incorporated by reference in entirety.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Further, the title, headings, terms and phrases used herein are not intended to limit the subject matter or scope; but rather, to provide an understandable description of the invention. The invention is composed of several sub-parts that serve a portion of the total functionality of the invention independently and contribute to system level functionality when combined with other parts of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

Any element in a claim that does not explicitly state "means for" performing a specific function, or "step for" performing a specific function, is not be interpreted as a "means" or "step" clause as specified in 35 U.S.C. Sec. 112, Paragraph 6. In particular, the use of "step of" in the claims herein is not intended to invoke the provisions of 35 U.S.C. Sec. 112, Paragraph 6.

Incorporation by Reference: All publications, patents, and patent applications mentioned in this specification are herein incorporated by reference to the same extent as if each individual publication, patent, or patent application was specifically and individually indicated to be incorporated by reference, including: US 2012/0305787A1 (Henson); U.S. Pat. No. 8,575,567B2 (Lyslo); U.S. Pat. No. 7,658,891B1 (Barnes); US 2005/0258378A1 (Speer).

We claim:
1. An apparatus for disinfection of air and surfaces, comprising:
a UV lamp having a mercury amalgam spot;
a power source;

a conduit body, which has at least one hole that is located near the mercury amalgam spot of the UV lamp; and an air moving device, which delivers air through the conduit body in a first direction; and the at least one hole directs the air in a second direction and near the mercury amalgam spot of the UV lamp;

the apparatus further comprises:

a computer system with a human machine interface (HMI);

a wireless communication controller communicates to the computer system;

whereby the air moving device provides cooling to alter the temperature near the mercury amalgam spot of the UV lamp, and the wireless communication controller controls the apparatus.

2. The apparatus of claim 1 wherein the computer system further comprises a programmable logic controller (PLC) and a computing device;

the wireless communication controller communicates to the programmable logic controller through the computing device;

the computing device is connected through hardwire to the programmable logic controller and the human machine interface using an Ethernet port on the programmable logic controller or a serial port or USB port or through a wireless router or an internet connected device.

3. The apparatus of claim 2, wherein the wireless communication controller uses Bluetooth Low Energy (BLE), low energy wireless communication or WiFi technology to communicate with the programmable logic controller; and the computing device of the apparatus has Ethernet, Bluetooth Low Energy and WiFi interfaces.

4. The apparatus of claim 2, wherein the computing device of the apparatus communicates with the programmable logic controller and the human machine interface, and the computing device of the apparatus uses commands specific to the programmable logic controller and the human machine interface.

5. The apparatus of claim 2, wherein the computing device of the apparatus is a single board computer (SBC).

6. The apparatus of claim 1, wherein at least one remote UV sensors is wirelessly connected to said apparatus and said wireless communication controller.

7. The apparatus of claim 1, wherein the wireless communication controller is a Smart Phone, a tablet, a handheld PC or a mobile computing device.

8. The apparatus of claim 1, wherein the apparatus transmits data to an Internet based server.

9. The apparatus of claim 1, wherein the wireless controller controls and displays the operating status of the UV apparatus.

10. The apparatus of claim 1, further comprising a dose verification device having at least one coupon, the at least one coupon having a UV sensitive portion, which can undergo a color change, in response to a UVC dose corresponding to a UVC wavelength range from 200 nm to 280 nm;

the at least one coupon has a UV dosage reference portion, which is calibrated to a certain UVC dose to achieve a level of disinfection for a target organism.

* * * * *